United States Patent
Hansen et al.

(10) Patent No.: US 12,304,970 B2
(45) Date of Patent: May 20, 2025

(54) NUCLEAR LOCALIZATION SIGNALS, COMPOSITIONS FORMED THEREFROM, AND METHODS OF USE THEREOF FOR DELIVERY OF CARGO TO THE NUCLEUS

(71) Applicant: Yale University, New Haven, CT (US)

(72) Inventors: James E. Hansen, Guilford, CT (US); Zahra Rattray, New Haven, CT (US)

(73) Assignee: YALE UNIVERSITY, New Haven, CT (US)

(*) Notice: Subject to any disclaimer, the term of this patent is extended or adjusted under 35 U.S.C. 154(b) by 1041 days.

(21) Appl. No.: 16/967,110

(22) PCT Filed: Feb. 1, 2019

(86) PCT No.: PCT/US2019/016296
§ 371 (c)(1),
(2) Date: Aug. 3, 2020

(87) PCT Pub. No.: WO2019/152806
PCT Pub. Date: Aug. 8, 2019

(65) Prior Publication Data
US 2021/0054102 A1    Feb. 25, 2021

Related U.S. Application Data

(60) Provisional application No. 62/625,198, filed on Feb. 1, 2018.

(51) Int. Cl.
*C07K 19/00* (2006.01)
*C07K 16/46* (2006.01)

(52) U.S. Cl.
CPC .......... *C07K 16/46* (2013.01); *C07K 2319/09* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,569,789 A | 2/1986 | Blattler | |
| 4,952,394 A | 8/1990 | Senter | |
| 5,137,877 A | 8/1992 | Kaneko | |
| 5,349,066 A | 9/1994 | Kaneko | |
| 5,618,528 A | 4/1997 | Cooper | |
| 2013/0225611 A1 | 8/2013 | Weis | |
| 2015/0376279 A1 | 12/2015 | Hansen | |

FOREIGN PATENT DOCUMENTS

| | | |
|---|---|---|
| EP | 3173428 | 5/2017 |
| WO | 1997032602 | 9/1997 |
| WO | 2008091911 | 7/2008 |
| WO | 2010056043 | 5/2010 |
| WO | 2011041721 | 4/2011 |
| WO | 2012135831 | 10/2012 |
| WO | 2012150543 | 11/2012 |
| WO | 2014130723 | 8/2014 |
| WO | 2016020892 | 2/2016 |
| WO | 2016033321 | 3/2016 |
| WO | 2019018426 | 1/2019 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Achuthan, et al., "Drug-induced Senescence Generates Chemoresistant Stemlike Cells with Low Reactive OxygenSpecies", J. Biol. Chem., 286(43):37813-37829 (2011).
Adams, et al., "Highly Specific in Vivo Tumor Targeting by Monovalent and Divalent Forms of 741F8 Anti-c-erbB-2 Single-Chain Fv1", Cancer Res., 53:4026-4034 (1993).
Alarcon-Segovia, et al., "Antibody penetration into living cells. I. Intranuclear immunoglobulin in peripheral blood mononuclear cells in mixed connective tissue disease and systemic lupus erythematosus", Clin Exp Immunol., 35(3):364-375 (1979).
Ambrus, et al., "Small molecule peptidomimetic inhibitors of importin a/b mediated nuclear transport", Bioorganic & Medicinal Chemistry, 18:7611-7620 (2010).
Axup, et al., "Synthesis of site-specific antibody-drug conjugates using unnatural amino acids", PNAS, 109(40): 16101-6 (2012).
Bachor, et al., "New method of peptide cleavage based on Edman degradation", Molecular diversity, 17 (3): 605-11 (2013).
Boswell-Casteel, et al., "Equilibrative nucleoside transporters—A review", Nucleosides Nucleotide Nucleic Acids, 36(1):7-30 (2017).
Cansizsoglu, et al., "Structure-based design of a pathway-specific nuclear import inhibitor", Nat. Struct. Mol. Biol., 14(5):452-454 (2007).

(Continued)

*Primary Examiner* — Christine J Saoud
*Assistant Examiner* — Jon M Lockard
(74) *Attorney, Agent, or Firm* — PABST PATENT GROUP LLP

(57) ABSTRACT

Amino acid sequences capable of enhancing nuclear translocation are provided. Also referred to a nuclear localization signals (NLS) the sequences can be linked to or grafted into antibodies or fragments or fusion proteins thereof to enhance nuclear translocation of the antibody. Compositions and antibodies including an NLS conjugated or otherwise linked directly or indirectly to an active agent cargo are also provided. Exemplary cargo includes proteins, peptides, carbohydrates, polysaccharides, nucleic acid molecules, inorganic molecules, organic molecules, and diagnostic agents. Pharmaceutical compositions further including a pharmaceutically acceptable carrier are also provided. Methods of delivering the composition or antibody alone or with a cargo linked thereto to the nucleus of cell, methods of selecting or screening for compositions having a desired cellular activity, and methods of treating diseases and disorders are also provided.

7 Claims, 2 Drawing Sheets
Specification includes a Sequence Listing.

(56) References Cited

OTHER PUBLICATIONS

Choi, et al., "A general strategy for generating intact, full-length IgG antibodies that penetrate into the cytosol of living cells", MABS, 6(6):1402-1414 (2017).
Chook, et al., "Nuclear import by Karyopherin-Bs: recognition and inhibition", Biochim. Biophys. Acta., 1813(9):1593-1606 (2011).
Chothia, et al., "Canonical Structures for the Hypervariable Regions of Immunoglobulins" J. Mol. Biol., 196:901-917 (1987).
Deng, et al., "In vivo cell penetration and intracellular transport of anti-Sm and anti-La autoantibodies", Int Immunol., 12(4):415-423 (2000).
Fahrenkrog, et al., "The nuclear pore complex: Nucleocytoplasmic transport and beyond", Nature Reviews Molecular Cell Biology, 4:757 (2003).
Freitas, et al., "Mechanisms and Signals for the Nuclear Import of Proteins", Current Genomics, 10(8):550-557 (2009).
Genbank AF289183.1 "Mus musculus anti-DNA monoclonal autoantibody G1-5 light chain variable region mRNA, partial cds", accessed Apr. 20, 2022.
GenBank: AAA65681.1, "immunoglobulin light chain, partial [Mus musculus]", accessed Apr. 20, 2022.
GenBank: L16981.1, "Mouse Ig rearranged L-chain gene, partial cds", Accessed Apr. 20, 2022.
Golan, et al., "Penetration of autoantibodies into living epithelial cells", J Invest Dermatol 100(3):316-322 (1993).
Gruber, et al., "Efficient tumor cell lysis mediated by a bispecific single chain antibody expressed in *Escherichia coli*", J. Immunol., 152(11):5368-5374 (1994).
Gu, et al., "Genetic determinants of autoimmune disease and coronary vasculitis in the MRL-Ipr/Ipr mouse model of systemic lupus erythematosus", J. Immunol., 161:6999-7006 (1998)).
Hansen, et al. "Antibody-mediated Hsp70 protein therapy", Brain Res., 1088(1): 187-96 (2006).
Hansen, et al., "Antibody-mediated p53 protein therapy prevents liver metastasis in vivo", Cancer Res, 67(4): 1769-74 (2007b).
Hansen, et al., "Intranuclear protein transduction through a nucleoside salvage pathway", J Biol Chem, 282(29):20790-20793 (2007a).
Hansen, et al., "Targeting cancer with a lupus autoantibody", Sci Transl Med., 4(157):157ra142 (2012).
Hintersteiner, et al., "Identification of a small molecule inhibitor of importin beta mediated nuclear import by confocal on-bead screening of tagged one-bead one-compound libraries", ACS Chem. Biol., 5(10):967979 (2010).
Hu, et al., "Minibody: A novel engineered anti-carcinoembryonic antigen antibody fragment (single-chain Fv-CH3) which exhibits rapid, high-level targeting of xenografts", Cancer Res., 56(13):3055-3061 (1996).
Im, et al., "Cell and nuclear penetrating anti-ds DNA autoantibodies have multiple arginines in CDR3 of VH and increase cellular level of pERK and Bcl2 in mesangial cells", Mol Immunol., 67:377-387 (2015).
Im, et al., "Development of single-chain Fv of antibody to DNA as intracellular delivery vehicle", Animal Cells and Systems, 21(6):382-387 (2017).
International Search Report for PCT/US2019/016296 dated May 13, 2019.
Isenberg, et al., "Detection of Cross-Reactive Anti-DNA Antibody Idiotypes in the Serum of Systemic Lupus Erythematosus Patients and of Their Relatives", Arthritis Rheum 28(9):999-1007 (1985).
Jacobson, et al., "An isotype switched and somatically mutated rheumatoid factor clone isolated from a MRL-Ipr/Ipr mouse exhibits limited intraclonal affinity maturation", The Journal of Immunology, 152(9):4489-4499 (1994).
Jang, et al., "A nucleic acid-hydrolyzing antibody penetrates into cells via caveolae-mediated endocytosis, localizes in the cytosol and exhibits cytotoxicity", Cell Mol Life Sci, 66(11-12):1985-97 (2009).

Kim, et al., "Heavy and Light Chain Variable Single Domains of an Anti-DNA Binding Antibody Hydrolyze Both Double-and Single-stranded DNAs without Sequence Specificity", J Biol Chem., 281(22):15287-95 (2006).
Kolodych, et al., "CBTF: new amine-to-thiol coupling reagent for preparation of antibody conjugates with increased plasma stability", Bioconjugate Chem., 26(2): 197-200 (2015).
Kostelny, et al., "Formation of a bispecific antibody by the use of leucine zippers", J. Immunol., 148(5):1547 (1992).
Kosugi, et al., "Design of Peptide Inhibitors for the Importin a/b Nuclear Import Pathway by Activity-Based Profiling", Chemistry & Biology, 15:940-949 (2008).
Kosugi, et al., "Systematic identification of cell cycle-dependent yeast nucleocytoplasmic shuttling proteins by prediction of composite motifs", PNAS, 106(25): 10171-10176 (2009).
Lee, et al., "Cell-penetrating autoantibody induces caspase-mediated apoptosis through catalytic hydrolysis of DNA", Biorg Med Chem., 15:2016-23 (2007).
Lundberg, et al., "Nuclear import and export inhibitors alter capsid protein distribution in mammalian cells and reduce Venezuelan Equine Encephalitis Virus replication", Antiviral Res, 100(3):662-672 (2013).
Lyon, et al., "Self-hydrolyzing maleimides improve the stability and pharmacological properties of antibody-drug conjugates", Bioconjugate Chem., 32(10): 1059-1062 (2014).
McCartney, et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides", Protein Eng., 8(3):301-14 (1995).
Noble, et al., "A nucleolytic lupus autoantibody is toxic to BRCA2-deficient cancer cells", Sci Rep., 4:5958 (2014).
Noble, et al., "DNA-damaging autoantibodies and cancer: the lupus butterfly theory", Nat. Rev. Rheumatol., 12(7):429-43 (2016).
Noble, et al., "Optimizing a lupus autoantibody for targeted cancer therapy", Cancer Research, 75(11):2285-2291 (2015).
Pack, et al., "Miniantibodies: use of amphipathic helices to produce functional, flexibly linked dimeric FV fragments with high avidity in *Escherichia coli*", Biochemistry, 31(6):1579-84 (1992).
Rahman, et al., "Systemic lupus erythematosus", N Engl J Med., 358(9):929-939 (2008).
Rattray, et al., "Re-Engineering and Evaluation of Anti-DNA Autoantibody 3E10 for Therapeutic Applications", Biochem Biophys Res Commun, 496: 858-864 (2018).
Rhodes, et al., "TRIM21 and the Function of Antibodies inside Cells", Trends Immunol., 38(12):916-926 (2017).
Sliwinska, et al., "Induction of senescence with doxorubicin leads to increased genomic instability of HCT116 cells", Mech. Ageing Dev., 130(1-2):24-32 (2009).
Soderholm et al., "Importazole, a small molecule inhibitor of the transport receptor importin-β", ACS Chem Biol 6(7):700-708 (2011).
Spertini, et al., "Idiotypic Vaccination with a Murine Anti-dsDNA Antibody: Phase I Study in Patients with Nonactive Systemic Lupus Erythematosus with nephritis", J. Rheumatol., 26(12): 2602-8 (1999).
Te Poele, et al., "DNA damage is able to induce senescence in tumor cells in vitro and in vivo", Cancer Res., 62(6):1876-1883 (2002).
Turchick, et al., "A cell-penetrating antibody inhibits human RAD51 via direct binding", Nucleic Acids Research, 45(20):11782-11799 (2017).
Van Der Watt, et al., "Targeting the Nuclear Import Receptor Kpnb1as an Anticancer Therapeutic", Mol Cancer Ther, 15(4):560-573 (2016).
Wagstaff, et al., "An AlphaScreen®-Based Assay for High-throughput Screening for Specific Inhibitors of nuclear Import", J Biomol Screen, 16(2): 192-200 (2011).
Wagstaff, et al., "Ivermectin is a specific inhibitor of importin α/β-mediated nuclear import able to inhibit replication of HIV-1 and dengue virus", Biochemical Journal, 443(3): 851-856 (2012).
Wang, et al., "Dipyridamole analogues as pharmacological inhibitors of equilibrative nucleoside transporters. Identification of novel potent and selective inhibitors of the adenosine transporter function of human equilibrative nucleoside transporter 4 (hENT4)", Biochem. Pharmacol., 86(11): 1-23(2013).

(56) References Cited

OTHER PUBLICATIONS

Wang, et al., "Nuclear import inhibitor N-(4-hydroxyphenyl) retinamide targets Zika virus (ZIKV) nonstructural protein 5 to inhibit ZIKV infection", Biochemical an Biophysical Research Communications, 493:1555-1559 (2017).
Weisbart, "Antibody-mediated transduction of p53 selectively kills cancer cells", Int. J. Oncol., 25(6):1867-1873 (2004).
Weisbart, et al., " Nuclear delivery of p53 C-terminal peptides into cancer cells using scFv fragments of a monoclonal antibody that penetrates living cells", Cancer Letters, 195(2): 211-219 (2003b).
Weisbart, et al., "A conserved anti-DNA antibody idiotype associated with nephritis in murine and human systemic lupus erythematosus", J Immunol., 144(7): 2653-2658 (1990).
Weisbart, et al., "An autoantibody is modified for use as a delivery system to target the cell nucleus: therapeutic implications", J. Autoimmun., 11(5):539-546 (1998).
Weisbart, et al., "Cell type specific targeted intracellular delivery into muscle of a monoclonal antibody that binds myosin IIb", Mol Immunol, 39(13):783-789 (2003a).
Weisbart, et al., "DNA-dependent targeting of cell nuclei by a lupus autoantibody", Sci Rep., 5(12022):1-6 (2015).
Weisbart, et al., "Novel protein transfection of primary rat cortical neurons using an antibody that penetrates living cells", J Immunol., 164(11): 6020-6026 (2000).
Wulbrand, et al., "Alpha-particle emitting 213Bi-anti-EGFR immunoconjugates eradicate tumor cells independent of oxygenation", PLoS One, 8 (5): e64730 (2013).
Yanase, et al., "Cellular Entry and Nuclear Localization of Anti-DNA Antibodies", Autoimmune Reactions, 19: 293-304 (1999).
Yanase, et al., "Receptor-mediated cellular entry of nuclear localizing anti-DNA antibodies via myosin 1", J. Clin. Invest., 100(1):25-31 (1997).
Ying-Chyi, et al., "Arginines in the CDR of anti-dsDNA autoantibodies facilitate cell internalization via electrostatic interactions", Eur J Immunol., 38(11):3178-3190 (2008).
Yu, et al., "Diagnostic criteria for systemic lupus erythematosus: a critical review", J Autoimmun., 48-49:10-3 (2014).
Zack, et al., "DNA mimics a self-protein that may be a target for some anti-DNA antibodies in systemic lupus erythematosus", J. Immunol., 154(4):1987-94 (1995).
Zack, et al., "Mechanisms of cellular penetration and nuclear localization of an anti-double strand DNA autoantibody", J Immunol., 157(5): 2082-2088 (1996).
Zack, et al., "Novel structural features of autoantibodies in murine lupus: a possible superantigen binding site?", Immunology and Cell Biology, 72:513-520 (1994).
Zhan, et al., "Recombinant Fv-Hsp70 protein mediates neuroprotection after focal cerebral ischemia in rats", Stroke: A Journal of Cerebral Circulation, 41(3):538-543 (2010).
Zhu, et al., "Remodeling domain interfaces to enhance heterodimer formation", Protein Sci., 6(4):781 (1997).
Aagaard et al., "RNAi therapeutics: Principles, prospects and challenges"Advanced Drug Delivery Reviews 59 75-86 (2007).

Blumberg et al., "Unraveling the autoimmune translational research process layer by layer" (Nat.; 18(1): 35-41) (2015).
Bork."Powers and Pitfalls in Sequences Analysis: The 70% Hurdle." Genome Research 10:398-400(2000).
Brown, et al., "Tolerance to Single, but Not Multiple, Amino Acid Replacements in Antibody Vh CDR2" Immunol. 156(9):3285-91(1996).
Burgess at al., Possible Dissociation of the Heparin-binding and Mitogenic Activites of Heparin-binding(Acidic Fibroblast) Growth Factor-1 from Its Receptor binding Activities by Site-directed Mutagenesis of a Single Lysine Residue. J. Cell Biol. 111:2129-2138. (1990).
Clark et al., Discovery and Development of Janus Kinase(KAK) Inhibitors for Inflammatory Diseases J. Med. Chem., 57(12) pp. 5023-5038 (2014).
Greenspan et al., Defining epitopes: It's not as easy as it seems; Nature Biotechology, 17:936-937(1999).
Guido et al., "Virtual Screening and Its Integration with Modern Drugs Design Technologies" Curr Med Chem. 2008 15(1) 34-46(2008).
Kulmanov et al., "DeepGO: predicting protein functions from sequence and interactions using a deep ontology-aware classifer"Bioinformatics, 34(4), 660-668(2018).
Lazar et al., Transforming Growth Factor alpha: Mutation of Aspartic Acid 47 and Leucine 48 Results in Different Biological Activities. Mol Cell. Biol., 8:1247-1252 (1988).
Ma."Animal Models of Disease" Modern Drug Discovery 7(6), 30-36 (2004).
McKeague et al., "Challenges and opportunities for small molecule aptamer Development" J Nucleic Acids. 2012:748913 EPub (2012).
Miosge, et al., "Comparison of predicted and actual consequences of missense mutations"Proc Natl Acad Sci USA 112(37) E5 189-98(2015.
Ola et al., "Importin beta: A novel autoantigen in human autoimmunity identified by screening random peptide libraries on phage." A Journal of Autoimmunity 26 197-207 (2006).
Skolnick et al.,"From Genes to Protein structure and function: novel applications of computational approaches in genomic era" Trends Biotechnol. 18(1): 34-9(2000.
Solderholm et al., ACS Chem Biol. 6, 700-708 (2011).
Steinman et al., "Optimization of current and future therapy for autoimmune diseases" Nat Med 6;18(1) 59-65 (2012).
Takahashi et al., DNA microarray analysis identifies NR4A2 as novel molecule involved in the pathogenesis of Sjogren's syndromeClinical and Experimental Immunology 190: 96-109 (2017).
Torok et al., "Pharmacogenetics of Crohn's disease" Pharmacogenomics 9(7) 881-893(2008).
Vajdos, et al., "Comprehensive functional maps of the antigen-binding site of am amti-ErbB2 antibody obtained with shotgun scanning mutagenesis", J Mol Biol., 320:415-28 (2002).
Warzocha et al., "Antisense Strategy: Biological Utility and Prospects in the Treatment of Hematological Malignancies" Leukemia and Lymphoma vol. 24 pp. 267-281 (1997).
Crump, Ivermectin: enigmatic multifaceted 'Wonder' drug continues to surprise and exceed expectations. 70. 495-505 (2017).

\* cited by examiner

SEQUENCE LISTING

```
<160> NUMBER OF SEQ ID NOS: 62

<210> SEQ ID NO 1
<211> LENGTH: 111
<212> TYPE: PRT
<213> ORGANISM: Mus musculus

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95
```

```
Glu Phe Pro Trp Thr Phe Gly Gly Gly Thr Lys Leu Glu Ile Lys
            100                 105                 110

<210> SEQ ID NO 2
<211> LENGTH: 111
<212> TYPE: PRT
<213> ORGANISM: Mus musculus

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 3
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 3

Arg Ala Ser Lys Ser Val Ser Thr Ser Ser Tyr Ser Tyr Met His
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Tyr Ala Ser Tyr Leu Glu Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Gln His Ser Arg Glu Phe Pro Trp Thr
1               5

<210> SEQ ID NO 6
<211> LENGTH: 116
<212> TYPE: PRT
<213> ORGANISM: Mus musculus

<400> SEQUENCE: 6
```

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 7

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Asp Tyr Gly Met His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide -continued

<400> SEQUENCE: 9

Asn Tyr Gly Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Tyr Ile Ser Ser Gly Ser Ser Thr Ile Tyr Tyr Ala Asp Thr Val Lys
1               5                   10                  15

Gly

<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 11

Arg Gly Leu Leu Leu Asp Tyr
1               5

<210> SEQ ID NO 12
<211> LENGTH: 274
<212> TYPE: PRT
<213> ORGANISM: Artificial Sequence
<220> FEATURE:
<223> OTHER INFORMATION: Synthetic Polypeptide

<400> SEQUENCE: 12

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
                20                  25                  30

Val Ser Thr Ser Ser Tyr Ser Tyr Met His Trp Tyr Gln Gln Lys Pro
            35                  40                  45

Gly Gln Pro Pro Lys Leu Leu Ile Lys Tyr Ala Ser Tyr Leu Glu Ser
        50                  55                  60

Gly Val Pro Ala Arg Phe Ser Gly Ser Gly Ser Gly Thr Asp Phe Thr
65                  70                  75                  80

Leu Asn Ile His Pro Val Glu Glu Asp Ala Ala Thr Tyr Tyr Cys
                85                  90                  95

Gln His Ser Arg Glu Phe Pro Trp Thr Phe Gly Gly Gly Thr Lys Leu
            100                 105                 110

Glu Ile Lys Arg Ala Asp Ala Ala Pro Gly Gly Gly Gly Ser Gly Gly
        115                 120                 125

Gly Gly Ser Gly Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
            180                 185                 190

Thr Ile Tyr Tyr Ala Asp Thr Val Lys Gly Arg Phe Thr Ile Ser Arg
            195                 200                 205

Asp Asn Ala Lys Asn Thr Leu Phe Leu Gln Met Thr Ser Leu Arg Ser
    210                 215                 220

Glu Asp Thr Ala Met Tyr Tyr Cys Ala Arg Arg Gly Leu Leu Leu Asp
225                 230                 235                 240

Tyr Trp Gly Gln Gly Thr Thr Leu Thr Val Ser Ser Leu Glu Gln Lys
                245                 250                 255

Leu Ile Ser Glu Glu Asp Leu Asn Ser Ala Val Asp His His His His
            260                 265                 270

His His

<210> SEQ ID NO 13
<211> LENGTH: 541
<212> TYPE: PRT
<213> ORGANISM: Artificial Sequence
<220> FEATURE:
<223> OTHER INFORMATION: Synthetic Polypeptide

<400> SEQUENCE: 13

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
        35                  40                  45

Gly Gln Pro Pro Lys Leu Leu Ile Lys Tyr Ala Ser Tyr Leu Glu Ser
    50                  55                  60

Gly Val Pro Ala Arg Phe Ser Gly Ser Gly Ser Gly Thr Asp Phe Thr
65                  70                  75                  80

Leu Asn Ile His Pro Val Glu Glu Asp Ala Ala Thr Tyr Tyr Cys
                85                  90                  95

Gln His Ser Arg Glu Phe Pro Trp Thr Phe Gly Gly Gly Thr Lys Leu
            100                 105                 110

Glu Ile Lys Arg Ala Asp Ala Ala Pro Gly Gly Gly Gly Ser Gly Gly
        115                 120                 125

Gly Gly Ser Gly Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
            180                 185                 190

Thr Ile Tyr Tyr Ala Asp Thr Val Lys Gly Arg Phe Thr Ile Ser Arg
        195                 200                 205

Asp Asn Ala Lys Asn Thr Leu Phe Leu Gln Met Thr Ser Leu Arg Ser
    210                 215                 220

Glu Asp Thr Ala Met Tyr Tyr Cys Ala Arg Arg Gly Leu Leu Leu Asp
225                 230                 235                 240

Tyr Trp Gly Gln Gly Thr Thr Leu Thr Val Ser Ser Ala Ser Thr Lys
                245                 250                 255

Gly Pro Ser Val Phe Pro Leu Ala Pro Leu Glu Ser Ser Gly Ser Asp
            260                 265                 270

```
Ile Val Leu Thr Gln Ser Pro Ala Ser Leu Ala Val Ser Leu Gly Gln
            275                 280                 285

Arg Ala Thr Ile Ser Cys Arg Ala Ser Lys Ser Val Ser Thr Ser Ser
        290                 295                 300

Tyr Ser Tyr Met His Trp Tyr Gln Gln Lys Pro Gly Gln Pro Pro Lys
305                 310                 315                 320

Leu Leu Ile Lys Tyr Ala Ser Tyr Leu Glu Ser Gly Val Pro Ala Arg
                325                 330                 335

Phe Ser Gly Ser Gly Ser Gly Thr Asp Phe Thr Leu Asn Ile His Pro
            340                 345                 350

Val Glu Glu Asp Ala Ala Thr Tyr Tyr Cys Gln His Ser Arg Glu
        355                 360                 365

Phe Pro Trp Thr Phe Gly Gly Gly Thr Lys Leu Glu Ile Lys Arg Ala
370                 375                 380

Asp Ala Ala Pro Gly Gly Gly Gly Ser Gly Gly Gly Ser Gly Gly
385                 390                 395                 400

Gly Gly Ser Glu Val Gln Leu Val Glu Ser Gly Gly Gly Leu Val Lys
                405                 410                 415

Pro Gly Gly Ser Arg Lys Leu Ser Cys Ala Ala Ser Gly Phe Thr Phe
                420                 425                 430

Ser Asn Tyr Gly Met His Trp Val Arg Gln Ala Pro Glu Lys Gly Leu
            435                 440                 445

Glu Trp Val Ala Tyr Ile Ser Ser Gly Ser Ser Thr Ile Tyr Tyr Ala
        450                 455                 460

Asp Thr Val Lys Gly Arg Phe Thr Ile Ser Arg Asp Asn Ala Lys Asn
465                 470                 475                 480

Thr Leu Phe Leu Gln Met Thr Ser Leu Arg Ser Glu Asp Thr Ala Met
                485                 490                 495

Tyr Tyr Cys Ala Arg Arg Gly Leu Leu Leu Asp Tyr Trp Gly Gln Gly
            500                 505                 510

Thr Thr Leu Thr Val Ser Ser Leu Glu Gln Lys Leu Ile Ser Glu Glu
        515                 520                 525

Asp Leu Asn Ser Ala Val Asp His His His His His
530                 535                 540

<210> SEQ ID NO 14
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Arg Gly Leu Leu Leu Asp Tyr Trp Gly Gln Gly Thr Thr Val
            100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 15

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 16
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 16

Glu Val Gln Leu Val Glu Ser Gly Gly Gly Asp Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 17
<211> LENGTH: 116
<212> TYPE: PRT
<213> ORGANISM: Artificial Sequence
```

<220> FEATURE:
<223> OTHER INFORMATION: Synthetic Polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 18

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 19

Glu Val Gln Leu Val Glu Ser Gly Gly Gly Asp Val Lys Pro Gly Gly
1               5                   10                  15

Ser Leu Arg Leu Ser Cys Ala Ser Gly Phe Thr Phe Ser Asn Tyr
            20                  25                  30

Gly Met His Trp Val Arg Gln Ala Pro Glu Lys Gly Leu Glu Trp Val
            35                  40                  45

Ser Tyr Ile Ser Ser Gly Ser Ser Thr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 20
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 20

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 21
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 21

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 23

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

```
Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 25

Asp Ile Gln Met Thr Gln Ser Pro Ser Ser Leu Ser Ala Ser Leu Gly
 1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 26
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 26

Asp Ile Gln Met Thr Gln Ser Pro Ser Ser Leu Ser Ala Ser Leu Gly
 1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125
```

```
Gly Gly Gly Ser Glu Val Gln Leu Val Glu Ser Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Leu Gly Asp Arg Ala Thr Ile
                275                 280                 285

Thr Cys Arg Ala Ser Lys Ser Val Ser Thr Ser Ser Tyr Ser Tyr Met
290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Ala Ala Thr Tyr Tyr Cys Gln His Ser Arg Glu Phe Pro Trp Thr
                355                 360                 365

Phe Gly Gly Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Gly Lys Gly Leu Glu Trp Val Ser
                435                 440                 445

Tyr Ile Ser Ser Ser Ser Thr Ile Tyr Tyr Ala Asp Ser Val Lys
450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
515

<210> SEQ ID NO 27
<211> LENGTH: 515
```

```
<212> TYPE: PRT
<213> ORGANISM: Artificial Sequence
<220> FEATURE:
<223> OTHER INFORMATION: Synthetic Polypeptide

<400> SEQUENCE: 27

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
            115                 120                 125

Gly Gly Gly Ser Glu Val Gln Leu Val Glu Ser Gly Gly Gly Val Val
        130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
        210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
        355                 360                 365

Phe Gly Gly Gly Thr Lys Val Glu Ile Lys Arg Ala Asp Ala Ala Pro
    370                 375                 380
```

Gly Gly Gly Ser Gly Gly Gly Ser Gly Gly Gly Ser Glu
385             390             395             400

Val Gln Leu Val Glu Ser Gly Gly Val Val Gln Pro Gly Gly Ser
            405             410             415

Leu Arg Leu Ser Cys Ala Ala Ser Gly Phe Thr Phe Ser Asn Tyr Gly
            420             425             430

Met His Trp Val Arg Gln Ala Pro Glu Lys Gly Leu Glu Trp Val Ser
        435             440             445

Tyr Ile Ser Ser Ser Ser Ser Thr Ile Tyr Tyr Ala Asp Ser Val Lys
    450             455             460

Gly Arg Phe Thr Ile Ser Arg Asp Asn Ser Lys Asn Thr Leu Tyr Leu
465             470             475             480

Gln Met Asn Ser Leu Arg Ala Glu Asp Thr Ala Val Tyr Tyr Cys Ala
            485             490             495

Arg Arg Gly Leu Leu Asp Tyr Trp Gly Gln Gly Thr Thr Val Thr
            500             505             510

Val Ser Ser
    515

<210> SEQ ID NO 28
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Thr Lys Val Glu Ile Lys Arg
            100                 105                 110

Ala Asp Ala Ala Pro Gly Gly Gly Gly Ser Gly Gly Gly Ser Gly
        115                 120                 125

Gly Gly Gly Ser Glu Val Gln Leu Val Glu Ser Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
            245                 250                 255

Phe Pro Leu Ala Pro Leu Glu Ser Ser Gly Ser Asp Ile Gln Met Thr
        260                 265                 270

Gln Ser Pro Ser Ser Leu Ser Ala Ser Leu Gly Asp Arg Ala Thr Ile
    275                 280                 285

Thr Cys Arg Ala Ser Lys Ser Val Ser Thr Ser Ser Tyr Ser Tyr Met
290                 295                 300

His Trp Tyr Gln Gln Lys Pro Gly Gln Pro Lys Leu Leu Ile Lys
305                 310                 315                 320

Tyr Ala Ser Tyr Leu Glu Ser Gly Val Pro Ser Arg Phe Ser Gly Ser
            325                 330                 335

Gly Ser Gly Thr Asp Phe Thr Leu Thr Ile Ser Ser Leu Gln Pro Glu
        340                 345                 350

Asp Ala Ala Thr Tyr Tyr Cys Gln His Ser Arg Glu Phe Pro Trp Thr
    355                 360                 365

Phe Gly Gly Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
            405                 410                 415

Leu Arg Leu Ser Cys Ala Ala Ser Gly Phe Thr Phe Ser Asn Tyr Gly
    420                 425                 430

Met His Trp Val Arg Gln Ala Pro Glu Lys Gly Leu Glu Trp Val Ser
435                 440                 445

Tyr Ile Ser Ser Ser Ser Thr Ile Tyr Tyr Ala Asp Ser Val Lys
            450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
            485                 490                 495

Arg Arg Gly Leu Leu Leu Asp Tyr Trp Gly Gln Gly Thr Thr Val Thr
        500                 505                 510

Val Ser Ser
        515

<210> SEQ ID NO 29
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 29

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Ser Gly Gly Gly Gly Ser Gly
        115                 120                 125

Gly Gly Gly Ser Glu Val Gln Leu Val Glu Ser Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ala Lys
                195                 200                 205

Asn Ser Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
275                 280                 285

Thr Cys Arg Ala Ser Lys Ser Val Ser Thr Ser Ser Tyr Ser Tyr Met
290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Phe Ala Thr Tyr Tyr Cys Gln His Ser Arg Glu Phe Pro Trp Thr
            355                 360                 365

Phe Gly Gln Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Gly Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
```

```
                       485                 490                 495
Arg Arg Gly Leu Leu Asp Tyr Trp Gly Gln Gly Thr Thr Val Thr
                500                 505                 510

Val Ser Ser
        515

<210> SEQ ID NO 30
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 30

Asp Ile Gln Met Thr Gln Ser Pro Ser Leu Ser Ala Ser Leu Gly
1               5                   10                  15

Asp Arg Ala Thr Ile Thr Cys Arg Ala Ser Lys Ser Val Ser Thr Ser
                20                  25                  30

Ser Tyr Ser Tyr Met His Trp Tyr Gln Gln Lys Pro Gly Gln Ala Pro
            35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
            115                 120                 125

Gly Gly Gly Ser Glu Val Gln Leu Val Glu Ser Gly Gly Gly Val Val
        130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
```

```
                    325                 330                 335
Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515

<210> SEQ ID NO 31
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 31

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Ser Gly
        115                 120                 125

Gly Gly Gly Ser Glu Val Gln Leu Val Glu Ser Gly Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
```

```
                    165                 170                 175
Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515
```

<210> SEQ ID NO 32
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 32

Asp Ile Gln Met Thr Gln Ser Pro Ser Ser Leu Ser Ala Ser Val Gly

-continued

```
1               5                   10                  15
Asp Arg Val Thr Ile Thr Cys Arg Ala Ser Lys Ser Val Ser Thr Ser
                20                  25                  30

Ser Tyr Ser Tyr Met His Trp Tyr Gln Gln Lys Pro Gly Lys Ala Pro
            35                  40                  45

Lys Leu Leu Ile Lys Tyr Ala Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
            165                 170                 175

Leu Glu Trp Val Ser Tyr Ile Ser Ser Ser Ser Thr Ile Tyr Tyr
        180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
            245                 250                 255

Phe Pro Leu Ala Pro Leu Glu Ser Ser Gly Ser Asp Ile Gln Met Thr
        260                 265                 270

Gln Ser Pro Ser Ser Leu Ser Ala Ser Val Gly Asp Arg Val Thr Ile
        275                 280                 285

Thr Cys Arg Ala Ser Lys Ser Val Ser Thr Ser Ser Tyr Ser Tyr Met
        290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
        370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430
```

Met His Trp Val Arg Gln Ala Pro Gly Lys Gly Leu Glu Trp Val Ser
            435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 33
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
                20                  25                  30

Ser Tyr Ser Tyr Met His Trp Tyr Gln Gln Lys Pro Gly Lys Ala Pro
            35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
            115                 120                 125

Gly Gly Gly Ser Glu Val Gln Leu Val Glu Ser Gly Gly Gly Val Val
        130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

-continued

Gln Ser Pro Ser Ser Leu Ser Ala Ser Val Gly Asp Arg Val Thr Ile
            275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515

<210> SEQ ID NO 34
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

```
Ala Asp Ala Ala Pro Gly Gly Gly Ser Gly Gly Gly Ser Gly
    115                 120                 125

Gly Gly Gly Ser Glu Val Gln Leu Val Glu Ser Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Val Gly Asp Arg Val Thr Ile
    275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Phe Ala Thr Tyr Tyr Cys Gln His Ser Arg Glu Phe Pro Trp Thr
    355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Glu Lys Gly Leu Glu Trp Val Ser
    435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
    515
```

<210> SEQ ID NO 35
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 35

```
Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Thr Val Ser Thr Ser Ser Tyr Ser Tyr Met
    290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
        355                 360                 365
```

```
Phe Gly Gly Gly Thr Lys Val Glu Ile Lys Arg Ala Asp Ala Ala Pro
    370                 375                 380

Gly Gly Gly Gly Ser Gly Gly Gly Ser Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Gly Lys Gly Leu Glu Trp Val Ser
            435                 440                 445

Tyr Ile Ser Ser Gly Ser Ser Thr Ile Tyr Tyr Ala Asp Ser Val Lys
    450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 36
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 36

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
                100                 105                 110

Ala Asp Ala Ala Pro Gly Gly Gly Gly Ser Gly Gly Gly Gly Ser Gly
            115                 120                 125

Gly Gly Gly Ser Glu Val Gln Leu Val Glu Ser Gly Gly Gly Val Val
130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ser Lys
    195                 200                 205
```

```
Asn Thr Leu Tyr Leu Gln Met Asn Ser Leu Arg Ala Glu Asp Thr Ala
    210                 215                 220
Val Tyr Tyr Cys Ala Arg Arg Gly Leu Leu Asp Tyr Trp Gly Gln
225                 230                 235                 240
Gly Thr Thr Val Thr Val Ser Ser Ala Ser Thr Lys Gly Pro Ser Val
                245                 250                 255
Phe Pro Leu Ala Pro Leu Glu Ser Ser Gly Ser Asp Ile Gln Met Thr
            260                 265                 270
Gln Ser Pro Ser Ser Leu Ser Ala Ser Leu Gly Asp Arg Ala Thr Ile
            275                 280                 285
Thr Cys Arg Ala Ser Lys Thr Val Ser Thr Ser Ser Tyr Ser Tyr Met
290                 295                 300
His Trp Tyr Gln Gln Lys Pro Gly Gln Pro Lys Leu Leu Ile Lys
305                 310                 315                 320
Tyr Ala Ser Tyr Leu Glu Ser Gly Val Pro Ser Arg Phe Ser Gly Ser
                325                 330                 335
Gly Ser Gly Thr Asp Phe Thr Leu Thr Ile Ser Ser Leu Gln Pro Glu
            340                 345                 350
Asp Ala Ala Thr Tyr Tyr Cys Gln His Ser Arg Glu Phe Pro Trp Thr
            355                 360                 365
Phe Gly Gly Gly Thr Lys Val Glu Ile Lys Arg Ala Asp Ala Ala Pro
370                 375                 380
Gly Gly Gly Gly Ser Gly Gly Gly Ser Gly Gly Gly Ser Glu
385                 390                 395                 400
Val Gln Leu Val Glu Ser Gly Gly Val Val Gln Pro Gly Gly Ser
                405                 410                 415
Leu Arg Leu Ser Cys Ala Ala Ser Gly Phe Thr Phe Ser Asn Tyr Gly
            420                 425                 430
Met His Trp Val Arg Gln Ala Pro Glu Lys Gly Leu Glu Trp Val Ser
    435                 440                 445
Tyr Ile Ser Ser Gly Ser Ser Thr Ile Tyr Tyr Ala Asp Ser Val Lys
    450                 455                 460
Gly Arg Phe Thr Ile Ser Arg Asp Asn Ser Lys Asn Thr Leu Tyr Leu
465                 470                 475                 480
Gln Met Asn Ser Leu Arg Ala Glu Asp Thr Ala Val Tyr Tyr Cys Ala
                485                 490                 495
Arg Arg Gly Leu Leu Asp Tyr Trp Gly Gln Gly Thr Thr Val Thr
            500                 505                 510
Val Ser Ser
        515

<210> SEQ ID NO 37
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 37

Asp Ile Gln Met Thr Gln Ser Pro Ser Ser Leu Ser Ala Ser Leu Gly
1               5                   10                  15
Asp Arg Ala Thr Ile Thr Cys Arg Ala Ser Lys Thr Val Ser Thr Ser
            20                  25                  30
Ser Tyr Ser Tyr Met His Trp Tyr Gln Gln Lys Pro Gly Gln Pro Pro
        35                  40                  45
```

```
Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Ala Ala Thr Tyr Tyr Cys Gln His Ser Arg
                 85                  90                  95

Glu Phe Pro Trp Thr Phe Gly Gly Gly Thr Lys Val Glu Ile Lys Arg
                100                 105                 110

Ala Asp Ala Ala Pro Gly Gly Gly Ser Gly Gly Gly Ser Gly
            115                 120                 125

Gly Gly Gly Ser Glu Val Gln Leu Val Glu Ser Gly Gly Gly Asp Val
130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
            275                 280                 285

Thr Cys Arg Ala Ser Lys Thr Val Ser Thr Ser Ser Tyr Ser Tyr Met
290                 295                 300

His Trp Tyr Gln Gln Lys Pro Gly Gln Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
            355                 360                 365

Phe Gly Gly Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
435                 440                 445

Tyr Ile Ser Ser Gly Ser Ser Thr Ile Tyr Tyr Ala Asp Ser Val Lys
450                 455                 460

Gly Arg Phe Thr Ile Ser Arg Asp Asn Ser Lys Asn Thr Leu Tyr Leu
```

```
            465                 470                 475                 480
Gln Met Asn Ser Leu Arg Ala Glu Asp Thr Ala Val Tyr Tyr Cys Ala
                    485                 490                 495

Arg Arg Gly Leu Leu Asp Tyr Trp Gly Gln Gly Thr Thr Val Thr
                500                 505                 510

Val Ser Ser
        515

<210> SEQ ID NO 38
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Lys Thr Val Ser Thr Ser Ser Tyr Ser Tyr Met
    290                 295                 300

His Trp Tyr Gln Gln Lys Pro Gly Lys Ala Pro Lys Leu Leu Ile Lys
```

```
              305                 310                 315                 320
Tyr Ala Ser Tyr Leu Glu Ser Gly Val Pro Ser Arg Phe Ser Gly Ser
            325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
            355                 360                 365

Phe Gly Gln Gly Thr Lys Val Glu Ile Lys Arg Ala Asp Ala Ala Pro
            370                 375                 380

Gly Gly Gly Gly Ser Gly Gly Gly Ser Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Gly Lys Gly Leu Glu Trp Val Ser
            435                 440                 445

Tyr Ile Ser Ser Gly Ser Ser Thr Ile Tyr Tyr Ala Asp Ser Val Lys
            450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
            485                 490                 495

Arg Arg Gly Leu Leu Leu Asp Tyr Trp Gly Gln Gly Thr Thr Val Thr
            500                 505                 510

Val Ser Ser
      515

<210> SEQ ID NO 39
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

Ser Tyr Ser Tyr Met His Trp Tyr Gln Gln Lys Pro Gly Lys Ala Pro
            35                  40                  45

Lys Leu Leu Ile Lys Tyr Ala Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
            85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Ser Gly
            115                 120                 125

Gly Gly Gly Ser Glu Val Gln Leu Val Glu Ser Gly Gly Gly Val Val
        130                 135                 140

Gln Pro Gly Gly Ser Leu Arg Leu Ser Cys Ala Ala Ser Gly Phe Thr
```

```
            145                 150                 155                 160
        Phe Ser Asn Tyr Gly Met His Trp Val Arg Gln Ala Pro Glu Lys Gly
                        165                 170                 175
        Leu Glu Trp Val Ser Tyr Ile Ser Ser Gly Ser Ser Thr Ile Tyr Tyr
                        180                 185                 190
        Ala Asp Ser Val Lys Gly Arg Phe Thr Ile Ser Arg Asp Asn Ser Lys
                        195                 200                 205
        Asn Thr Leu Tyr Leu Gln Met Asn Ser Leu Arg Ala Glu Asp Thr Ala
                        210                 215                 220
        Val Tyr Tyr Cys Ala Arg Arg Gly Leu Leu Leu Asp Tyr Trp Gly Gln
        225                 230                 235                 240
        Gly Thr Thr Val Thr Val Ser Ser Ala Ser Thr Lys Gly Pro Ser Val
                        245                 250                 255
        Phe Pro Leu Ala Pro Leu Glu Ser Ser Gly Ser Asp Ile Gln Met Thr
                        260                 265                 270
        Gln Ser Pro Ser Ser Leu Ser Ala Ser Val Gly Asp Arg Val Thr Ile
                        275                 280                 285
        Thr Cys Arg Ala Ser Lys Thr Val Ser Thr Ser Ser Tyr Ser Tyr Met
                290                 295                 300
        His Trp Tyr Gln Gln Lys Pro Gly Lys Ala Pro Lys Leu Leu Ile Lys
        305                 310                 315                 320
        Tyr Ala Ser Tyr Leu Glu Ser Gly Val Pro Ser Arg Phe Ser Gly Ser
                        325                 330                 335
        Gly Ser Gly Thr Asp Phe Thr Leu Thr Ile Ser Ser Leu Gln Pro Glu
                        340                 345                 350
        Asp Phe Ala Thr Tyr Tyr Cys Gln His Ser Arg Glu Phe Pro Trp Thr
                        355                 360                 365
        Phe Gly Gln Gly Thr Lys Val Glu Ile Lys Arg Ala Asp Ala Ala Pro
                        370                 375                 380
        Gly Gly Gly Gly Ser Gly Gly Gly Ser Gly Gly Gly Ser Glu
        385                 390                 395                 400
        Val Gln Leu Val Glu Ser Gly Gly Val Val Gln Pro Gly Gly Ser
                        405                 410                 415
        Leu Arg Leu Ser Cys Ala Ala Ser Gly Phe Thr Phe Ser Asn Tyr Gly
                        420                 425                 430
        Met His Trp Val Arg Gln Ala Pro Glu Lys Gly Leu Glu Trp Val Ser
                        435                 440                 445
        Tyr Ile Ser Ser Gly Ser Ser Thr Ile Tyr Tyr Ala Asp Ser Val Lys
                        450                 455                 460
        Gly Arg Phe Thr Ile Ser Arg Asp Asn Ser Lys Asn Thr Leu Tyr Leu
        465                 470                 475                 480
        Gln Met Asn Ser Leu Arg Ala Glu Asp Thr Ala Val Tyr Tyr Cys Ala
                        485                 490                 495
        Arg Arg Gly Leu Leu Leu Asp Tyr Trp Gly Gln Gly Thr Thr Val Thr
                        500                 505                 510
        Val Ser Ser
                515

<210> SEQ ID NO 40
<211> LENGTH: 515
<212> TYPE: PRT
<213> ORGANISM: Artificial Sequence
<220> FEATURE:
<223> OTHER INFORMATION: Synthetic Polypeptide
```

```
<400> SEQUENCE: 40

Asp Ile Gln Met Thr Gln Ser Pro Ser Leu Ser Ala Ser Val Gly
1               5                   10                  15

Asp Arg Val Thr Ile Thr Cys Arg Ala Ser Lys Thr Val Ser Thr
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Lys Thr Val Ser Thr Ser Ser Tyr Ser Tyr Met
    290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415
```

```
Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
            435                 440                 445

Tyr Ile Ser Ser Gly Ser Ser Thr Ile Tyr Tyr Ala Asp Ser Val Lys
            450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
            485                 490                 495

Arg Arg Gly Leu Leu Asp Tyr Trp Gly Gln Gly Thr Thr Val Thr
            500                 505                 510

Val Ser Ser
        515

<210> SEQ ID NO 41
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 41

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
            115                 120                 125

Gly Gly Gly Ser Glu Val Gln Leu Val Glu Ser Gly Gly Gly Leu Val
        130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255
```

Phe Pro Leu Ala Pro Leu Glu Ser Ser Gly Ser Asp Ile Gln Met Thr
                260                 265                 270

Gln Ser Pro Ser Ser Leu Ser Ala Ser Leu Gly Asp Arg Ala Thr Ile
            275                 280                 285

Thr Cys Arg Ala Ser Lys Thr Val Ser Thr Ser Ser Tyr Ser Tyr Met
290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Gly Lys Gly Leu Glu Trp Val Ser
        435                 440                 445

Tyr Ile Ser Ser Gly Ser Ser Thr Ile Tyr Tyr Ala Asp Ser Val Lys
450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Asp Tyr Trp Gly Gln Gly Thr Thr Val Thr
            500                 505                 510

Val Ser Ser
        515

<210> SEQ ID NO 42
<211> LENGTH: 112
<212> TYPE: PRT
<213> ORGANISM: Mus musculus

<400> SEQUENCE: 42

Asp Ile Val Leu Thr Gln Ser Pro Ala Ser Leu Ala Ala Val Ser Leu
1               5                   10                  15

Gly Glu Arg Ala Thr Ile Ser Tyr Arg Ala Ser Lys Ser Val Ser Thr
            20                  25                  30

Ser Gly Tyr Ser Tyr Met His Trp Asn Gln Gln Lys Pro Gly Gln Ala
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Asp Ala Ala Thr Tyr Tyr Cys Gln His Ile
                85                  90                  95

Arg Glu Leu Asp Thr Phe Phe Gly Gly Gly Thr Lys Leu Glu Ile Lys

<210> SEQ ID NO 43
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 43

Arg Ala Ser Lys Ser Val Ser Thr Ser Gly Tyr Ser Tyr Met His
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 44

Leu Val Ser Asn Leu Glu Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 45

Gln His Ile Arg Glu Leu Asp Thr Phe
1               5

<210> SEQ ID NO 46
<211> LENGTH: 120
<212> TYPE: PRT
<213> ORGANISM: Mus musculus

<400> SEQUENCE: 46

Gln Leu Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Ala Lys Arg Leu Glu Trp Val
        35                  40                  45

Ala Thr Ile Ser Ser Gly Gly Gly Ser Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ala Tyr Ser Lys Arg Gly Ala Met Asp Tyr Trp Gly Gln
            100                 105                 110

Gly Thr Ser Val Thr Val Ser Ser
        115                 120

<210> SEQ ID NO 47
<211> LENGTH: 5
<212> TYPE: PRT
<213> ORGANISM: Artificial Sequence
<220> FEATURE:

<223> OTHER INFORMATION: Synthetic Polypeptide

<400> SEQUENCE: 47

Ser Tyr Thr Met Ser
1               5

<210> SEQ ID NO 48
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 48

Thr Ile Ser Ser Gly Gly Gly Ser Thr Tyr Tyr Pro Asp Ser Val Lys
1               5                   10                  15

Gly

<210> SEQ ID NO 49
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 49

Arg Ala Tyr Ser Lys Arg Gly Ala Met Asp Tyr
1               5                   10

<210> SEQ ID NO 50
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 50

Arg Ala Ser Lys Ser Val Ser Thr Ser Ser Tyr Ser Tyr Met His Trp
1               5                   10                  15

Tyr Gln Gln Lys Pro Gly Gln Pro Pro Lys Leu Leu Ile Lys Tyr
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 51

Arg Ala Ser Lys Thr Val Ser Thr Ser Ser Tyr Ser Tyr Met His Trp
1               5                   10                  15

Tyr Gln Gln Lys Pro Gly Gln Pro Pro Lys Leu Leu Ile Lys Tyr
            20                  25                  30

<210> SEQ ID NO 52
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 52

Arg Val Thr Ile Thr Cys Arg Ala Ser Lys Ser Val Ser Thr Ser Ser
1               5                   10                  15

```
Tyr Ser Tyr Met His Trp Tyr Gln Gln Lys Pro Gly Lys Ala Pro Lys
            20                  25                  30
Leu

<210> SEQ ID NO 53
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: X = any amino acid, but preferentially is a
      basic amino acid (R or K).
<220> FEATURE:
<221> NAME/KEY: MISC_FEATURE
<222> LOCATION: (30)..(30)
<223> OTHER INFORMATION: X = any amino acid, but preferentially is a
      basic amino acid (R or K).

<400> SEQUENCE: 53

Xaa Arg Ala Ser Lys Thr Val Ser Thr Ser Ser Tyr Ser Tyr Met His
1               5                   10                  15

Trp Tyr Gln Gln Lys Pro Gly Gln Pro Pro Lys Leu Leu Xaa Lys Tyr
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 54

Arg Ala Ser Lys Ser Val Ser Thr Ser Asn Tyr Ser Tyr Met Tyr Trp
1               5                   10                  15

Tyr Gln Gln Lys Pro Gly Gln Pro Pro Lys Leu Leu Ile Lys Tyr
            20                  25                  30

<210> SEQ ID NO 55
<211> LENGTH: 113
<212> TYPE: PRT
<213> ORGANISM: Mus musculus

<400> SEQUENCE: 55

Asp Val Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Asn Tyr Met His Trp His Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His His Ser Arg
                85                  90                  95

Glu Phe Pro Trp Thr Phe Gly Gly Gly Thr Lys Leu Glu Ile Lys Arg
            100                 105                 110

Ala
```

```
<210> SEQ ID NO 56
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 56

Arg Ala Ser Lys Ser Val Ser Thr Ser Ser Tyr Asn Tyr Ile His Trp
1               5                   10                  15

His Gln Gln Lys Pro Gly Gln Pro Pro Lys Leu Leu Ile Lys Tyr
            20                  25                  30

<210> SEQ ID NO 57
<211> LENGTH: 113
<212> TYPE: PRT
<213> ORGANISM: Mus musculus

<400> SEQUENCE: 57

Asp Leu Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr His Met Tyr Thr Phe Gly Ser Gly Thr Lys Leu Glu Ile
            100                 105                 110

Lys

<210> SEQ ID NO 58
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 58

Lys Arg Pro Ala Ala Thr Lys Lys Ala Gly Gln Ala Lys Lys Lys Lys
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 59

Pro Lys Lys Lys Arg Lys Val
1               5

<210> SEQ ID NO 60
<211> LENGTH: 111
<212> TYPE: PRT
<213> ORGANISM: Artificial Sequence
<220> FEATURE:
```

<223> OTHER INFORMATION: Synthetic Polypeptide

<400> SEQUENCE: 60

```
Asp Ile Val Leu Thr Gln Ser Pro Ala Ser Leu Ala Val Ser Leu Gly
1               5                   10                  15

Gln Arg Ala Thr Ile Ser Arg Arg Ala Ser Lys Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Lys Lys Tyr Ala Ser Tyr Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Ile Lys
            100                 105                 110
```

<210> SEQ ID NO 61
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 61

```
Asp Ile Val Leu Thr Gln Ser Pro Ala Ser Leu Ala Val Ser Leu Gly
1               5                   10                  15

Gln Arg Ala Thr Ile Ser Arg Arg Ala Ser Lys Thr Val Ser Thr Ser
                20                  25                  30

Ser Tyr Ser Tyr Met His Trp Tyr Gln Gln Lys Pro Gly Gln Pro Pro
            35                  40                  45

Lys Leu Leu Lys Lys Tyr Ala Ser Tyr Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Ile Lys
            100                 105                 110
```

<210> SEQ ID NO 62
<211> LENGTH: 107
<212> TYPE: PRT
<213> ORGANISM: Mus musculus

<400> SEQUENCE: 62

```
Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Ser Ile Ser Asn Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Ile Ser Val Glu Thr
65                  70                  75                  80
```

-continued

```
Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
               100             105
```

NUCLEAR LOCALIZATION SIGNALS, COMPOSITIONS FORMED THEREFROM, AND METHODS OF USE THEREOF FOR DELIVERY OF CARGO TO THE NUCLEUS

CROSS-REFERENCE TO RELATED APPLICATION

This application is a National Phase application under 35 U.S.C. § 371 of International Application No. PCT/US2019/016296 filed on Feb. 1, 2019, which claims benefit of U.S. Provisional Application No. 62/625,198, filed Feb. 1, 2018, which, are hereby incorporated herein by reference in their entirety.

REFERENCE TO THE SEQUENCE LISTING

The Sequence Listing submitted as a text file named "YU_7384_PCT_ST25.txt," having a size of 109,663 bytes is hereby incorporated by reference pursuant to 37 C.F.R. § 1.52(e)(5).

FIELD OF THE INVENTION

This invention is generally related to compositions and methods of use thereof for increasing nuclear translocation of antibodies and the treatment of diseases and disorders associated thereof.

BACKGROUND OF THE INVENTION

Aberrant production of autoantibodies reactive against self-antigens results in inflammation and tissue damage that is characteristic of autoimmune diseases such as systemic lupus erythematosus (SLE), scleroderma, Sjogren's syndrome, Hashimoto's thyroiditis, multiple sclerosis, and many others. While most antibodies are targeted to extracellular antigens such as cell surface receptors or circulating factors, a select subset of autoantibodies has the unusual ability to penetrate into live cells where they can target intracellular antigens. For example, some nuclear antibodies (ANAs) penetrate live cells and localize to nuclei, and cause functional perturbations in autoimmune disease (Yanase and Madaio, in Autoimmune Reactions, S. Paul, Ed. (Humana Press, Totowa, N.J., 1999), pp. 293-304; Rhodes and Isenberg, *Trends Immunol* 38, 916-926 (2017); Ying-Chyi et al., *Eur J Immunol* 38, 3178-3190 (2008)). Anti-dsDNA antibodies are highly specific for systemic lupus erythematosus (SLE), and elevated titers are detected in ~70% of SLE patients, compared to 0.5% in healthy individuals or those presenting with other autoimmune disorders (e.g. rheumatoid arthritis) (Rahman and Isenberg, *N Engl J Med* 358, 929-939 (2008); Isenberg et al., *Arthritis Rheum* 28, 999-1007 (1985)). The specific contributions of anti-dsDNA antibodies to lupus pathophysiology are unknown, but these antibodies are included in the ACR (American College of Rheumatology) and SLICC (Systemic Lupus International Collaborating Clinics) SLE classification criteria, and are associated with dermatological and renal manifestations of lupus (Yu et al., *J Autoimmun* 48-49, 10-3 (2014)).

In particular, multiple cell and nuclear-penetrating lupus anti-DNA autoantibodies have been identified that are believed to contribute to the pathophysiology of SLE (and likely other autoimmune diseases) and in some cases to have the potential to be used as drug delivery vehicles or as single agents designed to perturb intracellular processes such as DNA repair (Noble et al., *Nat Rev Rheumatol* 12, 429-43 (2016)). For example, the murine anti-DNA autoantibody 3E10, isolated from the MRL/lpr lupus mouse model, has been shown to penetrate live cell nuclei, to localize to tumors due to its affinity for DNA released by dying cancer cells, and to inhibit DNA repair and thereby selectively kill cancer cells with defects in homology-directed repair (HDR) of DNA double-strand breaks (Hansen et al., *Sci Transl Med* 4(157):157ra142. doi: 10.1126/scitranslmed.3004385 (2012); Noble et al., *Cancer Res* 75, 2285-91 (2015); Weisbart et al., *Sci Rep* 5:12022. doi: 10.1038/srep12022. (2015)).

The mechanisms of cellular internalization by autoantibodies are diverse. Some are taken into cells through electrostatic interactions or FcR-mediated endocytosis, while others utilize mechanisms based on association with cell surface myosin or calreticulin, followed by endocytosis (Ying-Chyi et al., *Eur J Immunol* 38, 3178-3190 (2008), Yanase et al., *J Clin Invest* 100, 25-31 (1997)). 3E10 penetrates cells in an Fc-independent mechanism (as evidenced by the ability of 3E10 fragments lacking an Fc to penetrate cells) but requires presence of the nucleoside transporter ENT2 (Weisbart et al., *Sci Rep* 5:12022. doi: 10.1038/srep12022. (2015), Zack et al., *J Immunol* 157, 2082-2088 (1996), Hansen et al., *J Biol Chem* 282, 20790-20793 (2007)). In each of the above scenarios, although the method for crossing the cell membrane has been identified, the mechanism by which autoantibodies including 3E10 localize to cell nuclei remains elusive.

Thus, it is an object of the invention to identify the mechanism of nuclear localization of 3E10 and other nuclear penetrating antibodies, and to provide compositions and methods of use thereof, including diagnostic and therapeutic strategies, stemming therefrom.

SUMMARY OF THE INVENTION

Amino acid sequences capable of enhancing nuclear translocation are provided. Also referred to as nuclear localization signals (NLS) the sequences can be grafted or linked to antibodies or other proteins, or fragments and fusions thereof to enhance nuclear translocation of the antibody or protein. The antibody can be, for example, a monoclonal antibody, single chain variable fragments (scFv), di-scFv, tri-scFv, multi-scFv, diabody, triabody, tetrabody, disulfide-linked Fvs (sdFv), Fab', F(ab')$_2$, Fv, or single domain antibody fragment (sdAb).

The NLS can have an amino acid sequence of any one of SEQ ID NOS:50-53 or fragment and variant thereof that can translocate from the cytoplasm to the nucleus of a cell. For example, the NLS can have 70, 75, 80, 85, 90, 95, 96, 97, 98, or 99% sequence identity to any one of SEQ ID NOS:50-53. Typically, the composition or antibody does not have an amino acid sequence 100% identical to the light chain of murine antibodies 3E10, 5C6, G1-5, H241, or G2-6. In some embodiments, the composition or antibody does not have an amino acid sequence 100% identical to any one or more of SEQ ID NOs: 1, 2, 20-25, 42, and 54-56.

The NLS alone, or compositions and antibodies including the NLS can be conjugated or otherwise linked directly or indirectly to an active agent cargo are also provided. The cargo can be, for example, a protein, peptide, carbohydrate, polysaccharide, nucleic acid molecule, inorganic molecule, and organic molecule, or diagnostic agent.

Pharmaceutical compositions further including a pharmaceutically acceptable carrier are also provided. In some embodiments, the pharmaceutical composition includes one or more additional active agents (e.g., a therapeutic drug).

Methods of delivering to the nucleus of a cell compositions including the NLS is also provided. Typically, the methods include contacting the cell with a composition or antibody having an NLS conjugated or linked thereto, or grafted therein. Methods of selecting a composition or an antibody for a desired activity are also provided. The methods can include, for example, contacting the cells with a composition or antibody having an NLS conjugated or linked thereto, or grafted therein, testing the cell for a desired activity, and selecting the composition or antibody if the composition or antibody exhibits the desired activity. The method can be part of a screen wherein the selection method is repeated with various different compositions or antibodies. Any of the methods can be carried out with the composition or antibody alone or the composition or antibody having an active agent cargo conjugated or otherwise linked thereto. Thus in some embodiments, the NLS facilitates the delivery and/or selection of the composition or antibody alone, thus altering the activity of the composition or antibody absent the NLS. In some embodiments, the composition or antibody additionally or alternatively facilitates the delivery of a cargo into the nucleus, thus altering the activity of the cargo. The contacting can occur in vitro or in vivo. Non-limiting examples of the cellular activity for which the composition, antibody, or active agent can be selected or screened include enhanced cell growth, reduced cell growth, apoptosis, enhanced cell signaling or secretion of a particular type or generally, and reduced signaling or secretion of a particular type or generally.

Methods of treating subjects in need thereof are also provided. The methods typically include administering to a subject in need thereof an effective amount of a composition or antibody having an NLS conjugated or linked thereto, or grafted therein alone or with an active agent cargo conjugated or linked thereto. In some embodiments, the subject has cancer. Thus, methods of treating cancer including administering a subject with cancer a composition or antibody having an NLS conjugated or linked thereto, or grafted therein alone or with an active agent cargo conjugated or linked thereto are also provided.

Any of the methods can include delivery of one or more additional active agents. The additional active agents can be free from the composition or antibody having the NLS, and can be administered separately or together with the composition or antibody having the NLS. Thus, in some embodiments, the one or more additional active agents are administered in the same admixture as the composition or antibody having the NLS, while in some embodiments, they are administered to the subject in different admixtures at the same or at different times. In some embodiments, the one or more additional active agents is a conventional therapeutic agent for treating a disease or disorder harbored by the subject.

DETAILED DESCRIPTION OF THE INVENTION

I. Definitions

Figure 1:
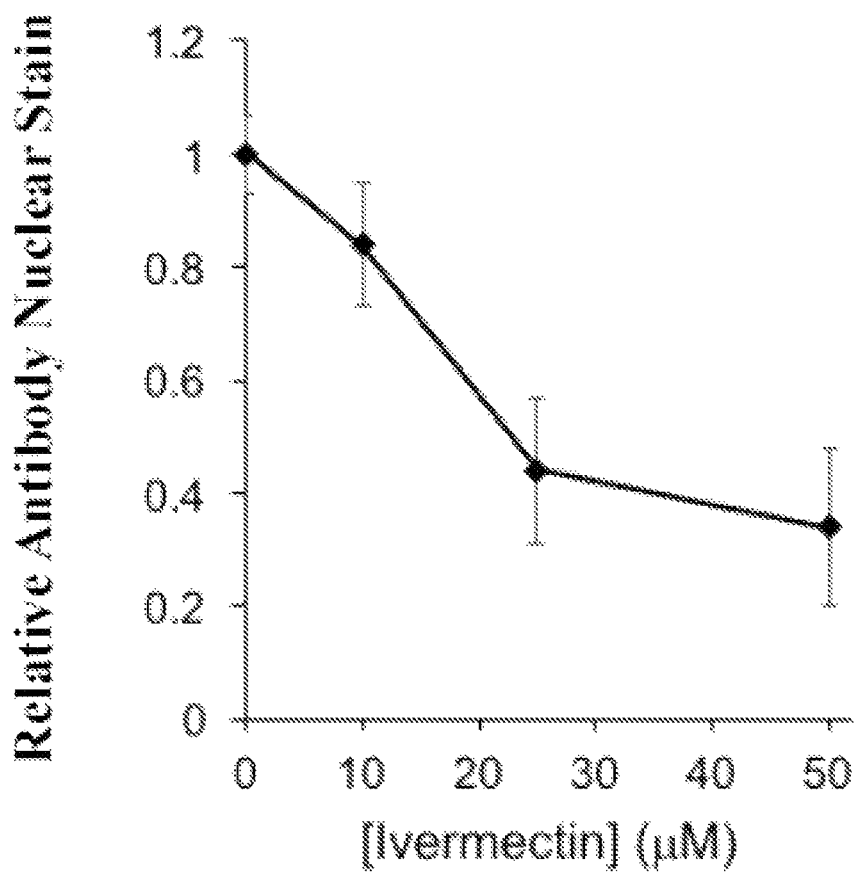
FIG. 1 is a line graph showing the relative intensity of variant 13 (compared to cells treated with variant 13 in the absence of ivermectin) nuclear staining in DLD1 cells co-incubated with varying concentrations of ivermectin.

The term "binding protein" is used in the context of the present disclosure to refer to human immunoglobulin molecules that bind and inhibit an importin disclosed herein and includes both polyclonal and monoclonal antibodies. The term also includes genetically engineered forms such as heteroconjugate antibodies (e.g., bispecific antibodies). The term "binding protein" also includes antigen binding forms of antibodies, including fragments with antigen-binding capability (e.g., Fab', F(ab')$_2$, Fab, Fv and rIgG as discussed in Pierce Catalogue and Handbook, 1994-1995 (Pierce Chemical Co., Rockford, Ill.); Kuby, J., Immunology, 3$^{rd}$ Ed., W.H. Freeman & Co., New York (1998). The term is also used to refer to recombinant single chain Fv fragments (scFv) as well as divalent (di-scFv) and trivalent (tri-scFV) forms thereof. The term antibody also includes bivalent or bispecific molecules, diabodies, triabodies, and tetrabodies. Examples of bivalent and bispecific molecules are described in Kostelny et al. (1992) J Immunol 148:1547; Pack and Pluckthun (1992) Biochemistry 31:1579; Hollinger et al., 1993, supra, Gruber et al. (1994) J. Immunol.:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

As used herein, the term "single chain Fv" or "scFv" as used herein means a single chain variable fragment that includes a light chain variable region ($V_L$) and a heavy chain variable region ($V_H$) in a single polypeptide chain joined by a linker which enables the scFv to form the desired structure for antigen binding (i.e., for the $V_H$ and $V_L$ of the single polypeptide chain to associate with one another to form a Fv). The $V_L$ and $V_H$ regions may be derived from the parent antibody or may be chemically or recombinantly synthesized.

As used herein, the term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917).

As used herein, the term "Framework Region" or "FR" residues are those variable domain residues other than the hypervariable region residues as herein defined.

As used herein, the term "antibody" refers to natural or synthetic antibodies that bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that bind the target antigen.

As used herein, the term "specifically binds" refers to the binding of an antibody to its cognate antigen (for example DNA) while not significantly binding to other antigens. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with that second molecule.

As used herein, the term "monoclonal antibody" or "MAb" refers to an antibody obtained from a substantially homogeneous population of antibodies, i.e., the individual antibodies within the population are identical except for possible naturally occurring mutations that may be present in a small subset of the antibody molecules.

As used herein, the term "DNA repair" refers to a collection of processes by which a cell identifies and corrects damage to DNA molecules. Single-strand defects are repaired by base excision repair (BER), nucleotide excision repair (NER), or mismatch repair (MMR). Double-strand breaks are repaired by non-homologous end joining (NHEJ), microhomology-mediated end joining (MMEJ), or homologous recombination. After DNA damage, cell cycle checkpoints are activated, which pause the cell cycle to give the cell time to repair the damage before continuing to divide. Checkpoint mediator proteins include BRCA1, MDC1, 53BP1, p53, ATM, ATR, CHK1, CHK2, and p21.

As used herein, the term "impaired DNA repair" refers to a state in which a mutated cell or a cell with altered gene expression is incapable of DNA repair or has reduced activity or efficiency of one or more DNA repair pathways or takes longer to repair damage to its DNA as compared to a wild type cell.

As used herein, the term "tumor" or "neoplasm" refers to an abnormal mass of tissue containing neoplastic cells. Neoplasms and tumors may be benign, premalignant, or malignant.

As used herein, the term "cancer" or "malignant neoplasm" refers to a cell that displays uncontrolled growth and division, invasion of adjacent tissues, and often metastasizes to other locations of the body.

As used herein, the term "inhibit" means to decrease an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, the term "fusion protein" refers to a polypeptide formed by the joining of two or more polypeptides through a peptide bond formed between the amino terminus of one polypeptide and the carboxyl terminus of another polypeptide or through linking of one polypeptide to another through reactions between amino acid side chains (for example disulfide bonds between cysteine residues on each polypeptide). The fusion protein can be formed by the chemical coupling of the constituent polypeptides or it can be expressed as a single polypeptide from a nucleic acid sequence encoding the single contiguous fusion protein. Fusion proteins can be prepared using conventional techniques in molecular biology to join the two genes in frame into a single nucleic acid sequence, and then expressing the nucleic acid in an appropriate host cell under conditions in which the fusion protein is produced.

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or includes a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "sustained release" refers to release of a substance over an extended period of time in contrast to a bolus type administration in which the entire amount of the substance is made biologically available at one time.

As used herein, the phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

As used herein, the term "individual," "host," "subject," and "patient" are used interchangeably to refer to any individual who is the target of administration or treatment. The subject can be a vertebrate, for example, a mammal Thus, the subject can be a human or veterinary patient.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "active agent" refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The term "subject" or "patient" refers to any individual who is the target of administration. The subject can be a vertebrate, for example, a mammal. Thus, the subject can be a human. The subject can be domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators.

Zoo- or circus-maintained animals include, for example, lions, tigers, bears, camels, giraffes, hippopotamuses, and rhinoceroses. The term does not denote a particular age or sex.

One of skill in the art will appreciate that the "importin pathway" transports protein molecules into the nucleus by binding to specific recognition sequences, called nuclear localization sequences (NLS). Importin has two general subunits, importin α and importin β which represent and/or interact with a larger family of proteins comprising importin-4, importin-5, importin-7, importin-8, importin-9, importin-11, importin-13, importin-α1, importin-α2, importin-α3, importin-α4, importin-α5, importin-α6 and importin-β1, importin-β2, a nucleoporin, a Ran protein. Accordingly, in an example, an inhibitor of the importin pathway encompassed by the present disclosure inhibits one or both of importin α and importin β. In another example, an inhibitor of the importin pathway encompassed by the present disclosure inhibits one or more of importin-4, importin-5, importin-7, importin-8, importin-9, importin-11, importin-13, importin-α1, importin-α2, importin-α3, importin-α4, importin-α5, importin-α6 and importin-β1, importin-β2, a nucleoporin, a Ran protein. Thus an inhibitor of the importin pathway can inhibit a structure or function of the nuclear pore. In another example, an importin inhibitor encompassed by the present disclosure inhibits expression of a gene encoding an above referenced importin or other importin pathway or nuclear pore protein. For example, an importin inhibitor can inhibit expression of one or more of IPO4, IPO5, IPO7, IPO11, IPO13, KPNA1, KPNA2, KPNA3, KPNA4, KPNA5, KPNA6, KPNB1 and TNPO1.

As used herein, the term "nuclear penetrating antibody" refers to an antibody, or antigen binding fragment or molecule thereof that is transported into the nucleus of living mammalian cells and binds to a target therein (e.g., a nuclear localized ligand). Exemplary targets include, but are not limited proteins and nucleic acids. An antibody that binds to DNA (e.g., single-stranded and/or double-stranded DNA) can be referred to as an anti-DNA antibody. In some embodiments, a nuclear penetrating antibody is transported into the nucleus of a cell without the aid of a carrier or conjugate. In another embodiment, a nuclear penetrating antibody is conjugated to a cell and/or nuclear-penetrating moiety, such as a cell penetrating peptide. One of skill in the art will appreciate that the term "nuclear penetrating" can be used in the context of the present disclosure to refer to other particles having a targeting moiety that targets a nuclear ligand such as scFv. For example, the term can be used to refer to a scFv that is transported into the nucleus of a cell without the aid of a carrier or conjugate and binds a nuclear ligand (e.g., single-stranded and/or double-stranded DNA, RNA, protein, etc.).

II. Compositions

A range of humanized 3E10 variants were generated with subtle differences in framework and CDR sequences. In evaluating the ability of these variants to carry out the original functions of 3E10 (D31N) di-scFv, a select number of the variants were found to penetrate cell nuclei more efficiently than the original 3E10 (D31N) di-scFv, while others were found to have lost the ability to penetrate nuclei. The subsections below provide sequences for murine 3E10 antibody heavy and light chains and humanized variants thereof, sequences for murine 5C6 heavy and light chains, and the putative nuclear localization signals (NLS) identified therein. Also provided are compounds into which a nuclear localization signals can be grafted or onto which they can be conjugated. Optionally additional active agent cargos, and pharmaceutical compositions including these compounds with improved nuclear penetration are also disclosed.

A. Antibody Sequences

Select anti-DNA antibodies can penetrate into live cell nuclei and inhibit DNA repair or directly damage DNA, and efforts to use these antibodies against tumors that are sensitive to DNA damage are underway (Hansen, et al., *Sci Transl Med*, 4(157):157ra142 (2012), Noble, et al., *Cancer Research*, 2015; 75(11):2285-2291, Noble, et al., *Sci Rep-Uk*, 4 (2014), Noble, et al., *Nat Rev Rheumatol* (2016)).

A panel of hybridomas, including the 3E10 and 5C6 hybridomas was previously generated from the MRLmpj/lpr lupus mouse model and DNA binding activity was evaluated (Zack, et al., *J. Immunol.* 154:1987-1994 (1995); Gu, et al., *J. Immunol.*, 161:6999-7006 (1998)).

1. 3E10

In the early 1990s a murine lupus anti-DNA antibody, 3E10, was tested in experimental vaccine therapy for SLE. These efforts were aimed at developing anti-idiotype antibodies that would specifically bind anti-DNA antibody in SLE patients. However, 3E10 was serendipitously found to penetrate into living cells and nuclei without causing any observed cytotoxicity (Weisbart R H, et al. *J Immunol*. 1990 144(7): 2653-2658; Zack D J, et al. *J Immunol*. 1996 157(5): 2082-2088). Studies on 3E10 in SLE vaccine therapy were then supplanted by efforts focused on development of 3E10 as a molecular delivery vehicle for transport of therapeutic molecules into cells and nuclei. 3E10 preferentially binds DNA single-strand tails, inhibits key steps in DNA single-strand and double-strand break repair (Hansen, et al., *Science Translational Medicine*, 4:157ra142 (2012)). 3E10 can have a $V_H$ having an amino acid sequence as shown in SEQ ID NO:6 or 7 and a $V_L$ having an amino acid sequence as shown in SEQ ID NO:1 or 2. The 3E10 antibody and its single chain variable fragment which includes a D31N mutation in CDR1 of the $V_H$ (3E10 (D31N) scFv) and di- and tri-valent fusions thereof penetrate into cells and nuclei and have proven capable of transporting therapeutic protein cargoes attached to the antibody either through chemical conjugation or recombinant fusion. Protein cargos delivered to cells by 3E10 or 3E10 (D31N) scFv include catalase, p53, and Hsp70 (Weisbart R H, et al. *J Immunol.* 2000 164: 6020-6026; Hansen J E, et al. *Cancer Res.* 2007 Feb. 15; 67(4): 1769-74; Hansen J E, et al. *Brain Res.* 2006 May 9; 1088(1): 187-96). 3E10 (D31N) scFv effectively mediated delivery of Hsp70 to neurons in vivo and this resulted in decreased cerebral infarct volumes and improved neurologic function in a rat stroke model (Zhan X, et al. *Stroke.* 2010 41(3): 538-43).

3E10 and 3E10 (D31N) scFv and di- and tri-valent fusions thereof, without being conjugated to any therapeutic protein, enhance cancer cell radiosensitivity and chemosensitivity and this effect is potentiated in cells deficient in DNA repair. Moreover, 3E10 and 3E10 scFv and di- and tri-valent fusions thereof are selectively lethal to cancer cells deficient in DNA repair even in the absence of radiation or chemotherapy. The Food and Drug Administration (FDA) has established a pathway for the development of monoclonal antibodies into human therapies, and 3E10 has already been approved by the FDA for use in a Phase I human clinical trial designed to test the efficacy of 3E10 in experimental vaccine therapy for SLE (Spertini F, et al. *J Rheumatol.* 1999 26(12): 2602-8).

Experiments indicate that 3E10 (D31N) scFv penetrates cell nuclei by first binding to extracellular DNA or its degradation products and then following them into cell nuclei through the ENT2 nucleoside salvage pathway (Weisbart, *Scientific Reports,* 5:Article number: 12022 (2015) doi:10.1038/srep12022). When administered to mice and rats 3E10 is preferentially attracted to tissues in which extracellular DNA is enriched, including tumors, regions of ischemic brain in stroke models, and skeletal muscle subject to contractile injury (Weisbart, et al., *Sci Rep.,* 5:12022 (2015), Hansen, et al., *J Biol Chem,* 282(29):20790-20793 (2007), Weisbart, et al., *Mol Immunol,* 39(13):783-789 (2003), Zhan, et al., *Stroke: A Journal of Cerebral Circulation,* 41(3):538-543 (2010)). Thus the presence of extracellular DNA enhances the nuclear uptake of 3E10 (D31N) scFv. Furthermore, 3E10 (D31N) scFv preferentially localizes into tumor cell nuclei in vivo, likely due to increased DNA in the local environment released from ischemic and necrotic regions of tumor.

3E10 Antibody Sequences

3E10 can refer to a monoclonal antibody produced by ATCC Accession No. PTA 2439 hybridoma. Mouse and exemplary humanized 3E10 antibody sequences are provided below.

a. 3E10 Light Chain Variable Region

An amino acid sequence for the light chain variable region of 3E10 can be, for example, (SEQ ID NO: 1)
DIVLTQSPASLAVSLGQRATISCRASKSVSTSSYSYMHWYQQKPGQP

PKLLIKYASYLESGVPARFSGSGSGTDFTLNIHPVEEEDAATYYCQH

SREFPWTFGGGTKLEIK,
or (SEQ ID NO: 2)
DIVLTQSPASLAVSLGQRATISCRASKSVSTSSYSYMHWYQQKPGQP

PKLLIKYASYLESGVPARFSGSGSGTDFHLNIHPVEEEDAATYYCQH

SREFPWTFGGGTKLELK.

In some embodiments, the complementarity determining regions (CDRs) are defined accordingly to the underlining above (e.g.,

```
CDR L1:
                                     (SEQ ID NO: 3)
RASKSVSTSSYSYMH;

CDR L2:
                                     (SEQ ID NO: 4)
YASYLES;

CDR L3:
                                     (SEQ ID NO: 5)
QHSREFPWT).
```

Other 3E10 light chain sequences are known in the art. See, for example, Zack, et al., *J. Immunol.,* 15; 154(4):1987-94 (1995); GenBank: L16981.1—*Mouse Ig rearranged L-chain gene, partial cds*; GenBank: AAA65681.1—*immunoglobulin light chain, partial [Mus musculus]*).

b. 3E10 Heavy Chain Variable Region

An amino acid sequence for the heavy chain variable region of 3E10 is:

(SEQ ID NO: 6)
EVQLVESGGGLVKPGGSRKLSCAASGFTFS*D*YGMHWVRQAPEKGLE

WVAYISSGSSTIYYADTVKGRFTISRDNAKNTLFLQMTSLRSEDTA

MYYCARRGLLLDYWGQGTTLTVSS;

Zack, et al., *Immunology and Cell Biology,* 72:513-520 (1994); GenBank: L16981.1—*Mouse Ig rearranged L-chain gene, partial cds*; and GenBank: AAA65679.1—*immunoglobulin heavy chain, partial [Mus musculus]*).

An amino acid sequence for a preferred variant of the heavy chain variable region of 3E10 is:

(SEQ ID NO: 7)
EVQLVESGGGLVKPGGSRKLSCAASGFTFS*N*YGMHWVRQAPEKGLE

WVAYISSGSSTIYYADTVKGRFTISRDNAKNTLFLQMTSLRSEDTA

MYYCARRGLLLDYWGQGTTLTVSS.

Amino acid position 31 of the heavy chain variable region of 3E10 has been determined to be influential in the ability of the antibody and fragments thereof to penetrate nuclei and bind to DNA. For example, D31N mutation (bolded and italicized in SEQ ID NOS:6 and 7) in CDR1 penetrates nuclei and binds DNA with much greater efficiency than the original antibody (Zack, et al., *Immunology and Cell Biology,* 72:513-520 (1994), Weisbart, et al., *J. Autoimmun.,* 11, 539-546 (1998); Weisbart, *Int. J. Oncol.,* 25, 1867-1873 (2004)).

In some embodiments, the complementarity determining regions (CDRs) are defined accordingly to the underlining above (e.g., (original sequence):

```
CDR H1.1 (original sequence):
                                     (SEQ ID NO: 8)
DYGMH;

CDR H1.2 (with D31N mutation):
                                     (SEQ ID NO: 9)
NYGMH;

CDR H2:
                                     (SEQ ID NO: 10)
YISSGSSTIYYADTVKG;

CDR H3:
                                     (SEQ ID NO: 11)
RGLLLDY.
``` c. Exemplary Mouse scFv

An exemplary mouse 3E10 scFv can have the sequence:

(SEQ ID NO: 12)
AGIHDIVLTQSPASLAVSLGQRATISCRASKSVSTSSYSYMHWYQQKP

GQPPKLLIKYASYLESGVPARFSGSGSGTDFTLNIHPVEEEDAATYYC

QHSREFPWTFGGGTKLEIKRADAAPGGGGSGGGGSGGGGSEVQLVESG

GGLVKPGGSRKLSCAASGFTFSNYGMHWVRQAPEKGLEWVAYISSG

SSTIYYADTVKGRFTISRDNAKNTLFLQMTSLRSEDTAMYYCARRGLL

LDYWGQGTTLTVSSLEQKLISEEDLNSAVDHHHHHH

An exemplary mouse 3E10 di-scFv can have the sequence:

```
                                        (SEQ ID NO: 13)
AGIHDIVLTQSPASLAVSLGQRATISCRASKSVSTSSYSYMHWYQQK

PGQPPKLLIKYASYLESGVPARFSGSGSGTDFTLNIHPVEEEDAATYY

CQHSREFPWTFGGGTKLEIKRADAAPGGGGSGGGGSGGGGSEVQLV

ESGGGLVKPGGSRKLSCAASGFTFSNYGMHWVRQAPEKGLEWVAYI

SSGSSTIYYADTVKGRFTISRDNAKNTLFLQMTSLRSEDTAMYYCAR

RGLLLDYWGQGTTLTVSSASTKGPSVFPLAPLESSGSDIVLTQSPASL

AVSLGQRATISCRASKSVSTSSYSYMHWYQQKPGQPPKLLIKYASYL

ESGVPARFSGSGSGTDFTLNIHPVEEEDAATYYCQHSREFPWTFGGG

TKLEIKRADAAPGGGGSGGGGSGGGGSEVQLVESGGGLVKPGGSRK

LSCAASGFTFSNYGMHWVRQAPEKGLEWVAYISSGSSTIYYADTVK

GRFTISRDNAKNTLFLQMTSLRSEDTAMYYCARRGLLLDYWGQGTT

LTVSSLEQKLISEEDLNSAVDHHHHHH
``` d. Exemplary Humanized 3E10 Variants

```
Heavy Chain variable region (variants 2, 6 and 10)
                                        SEQ ID NO: 14
EVQLVESGGGLVQPGGSLRLSCAASGFTFSNYGMHWVRQAPGKGLE

WVSYISSSSSTIYYADSVKGRFTISRDNAKNSLYLQMNSLRAEDTAV

YYCARRGLLLDYWGQGTTVTVSS

Heavy Chain variable region (variants 3, 7 and 11)
                                        SEQ ID NO: 15
EVQLVESGGGVVQPGGSLRLSCAASGFTFSNYGMHWVRQAPEKGLE

WVSYISSSSSTIYYADSVKGRFTISRDNSKNTLYLQMNSLRAEDTAVY

YCARRGLLLDYWGQGTTVTVSS

Heavy Chain variable region (variants 4, 8 and 12)
                                        SEQ ID NO: 16
EVQLVESGGGDVKPGGSLRLSCAASGFTFSNYGMHWVRQAPEKGLE

WVSYISSSSSTIYYADSVKGRFTISRDNSKNTLYLQMNSLRAEDTAVY

YCARRGLLLDYWGQGTTVTVSS

Heavy Chain variable region (variants 13, 16 and 19)
                                        SEQ ID NO: 17
EVQLVESGGGLVQPGGSLRLSCAASGFTFSNYGMHWVRQAPGKGLE

WVSYISSGSSTIYYADSVKGRFTISRDNAKNSLYLQMNSLRAEDTAV

YYCARRGLLLDYWGQGTTVTVSS

Heavy Chain variable region (variants 14 and 17)
                                        SEQ ID NO: 18
EVQLVESGGGVVQPGGSLRLSCAASGFTFSNYGMHWVRQAPEKGLE

WVSYISSGSSTIYYADSVKGRFTISRDNSKNTLYLQMNSLRAEDTAV

YYCARRGLLLDYWGQGTTVTVSS

Heavy Chain variable region (variants 15 and 18)
                                        SEQ ID NO: 19
EVQLVESGGGDVKPGGSLRLSCAASGFTFSNYGMHWVRQAPEKGLE

WVSYISSGSSTIYYADSVKGRFTISRDNSKNTLYLQMNSLRAEDTAV

YYCARRGLLLDYWGQGTTVTVSS

Light Chain variable region (variants 2, 3 and 4)
                                        SEQ ID NO: 20
DIQMTQSPSSLSASLGDRATITCRASKSVSTSSYSYMHWYQQKPGQP

PKLLIKYASYLESGVPSRFSGSGSGTDFTLTISSLQPEDAATYYCQHSR

EFPWTFGGGTKVEIK

Light Chain variable region (variants 6, 7 and 8)
                                        SEQ ID NO: 21
DIQMTQSPSSLSASLGDRATITCRASKSVSTSSYSYMHWYQQKPGQA

PKLLIKYASYLESGVPSRFSGSGSGTDFTLTISSLQPEDFATYYCQHSR

EFPWTFGQGTKVEIK

Light Chain variable region (variants 10, 11 and 12)
                                        SEQ ID NO: 22
DIQMTQSPSSLSASVGDRVTITCRASKSVSTSSYSYMHWYQQKPGKA

PKLLIKYASYLESGVPSRFSGSGSGTDFTLTISSLQPEDFATYYCQHSR

EFPWTFGQGTKVEIK

Light Chain variable region (variants 13, 14 and 15)
                                        SEQ ID NO: 23
DIQMTQSPSSLSASLGDRATITCRASKTVSTSSYSYMHWYQQKPGQP

PKLLIKYASYLESGVPSRFSGSGSGTDFTLTISSLQPEDAATYYCQHSR

EFPWTFGGGTKVEIK

Light Chain variable region (variants 16, 17 and 18)
                                        SEQ ID NO: 24
DIQMTQSPSSLSASVGDRVTITCRASKTVSTSSYSYMHWYQQKPGKA

PKLLIKYASYLESGVPSRFSGSGSGTDFTLTISSLQPEDFATYYCQHSR

EFPWTFGQGTKVEIK

Light Chain variable region (variant 19)
                                        SEQ ID NO: 25
DIQMTQSPSSLSASLGDRATITCRASKTVSTSSYSYMHWYQQKPGQA

PKLLIKYASYLESGVPSRFSGSGSGTDFTLTISSLQPEDFATYYCQHSR

EFPWTFGQGTKVEIK

Variant 2
                                        SEQ ID NO: 26
DIQMTQSPSSLSASLGDRATITCRASKSVSTSSYSYMHWYQQKPGQP

PKLLIKYASYLESGVPSRFSGSGSGTDFTLTISSLQPEDAATYYCQHSR

EFPWTFGGGTKVEIKRADAAPGGGGSGGGGSGGGGSEVQLVESGGG

LVQPGGSLRLSCAASGFTFSNYGMHWVRQAPGKGLEWVSYISSSSST

IYYADSVKGRFTISRDNAKNSLYLQMNSLRAEDTAVYYCARRGLLL

DYWGQGTTVTVSSASTKGPSVFPLAPLESSGSDIQMTQSPSSLSASLG

DRATITCRASKSVSTSSYSYMHWYQQKPGQPPKLLIKYASYLESGVP

SRFSGSGSGTDFTLTISSLQPEDAATYYCQHSREFPWTFGGGTKVEIK

RADAAPGGGGSGGGGSGGGGSEVQLVESGGGLVQPGGSLRLSCAAS

GFTFSNYGMHWVRQAPGKGLEWVSYISSSSSTIYYADSVKGRFTISR

DNAKNSLYLQMNSLRAEDTAVYYCARRGLLLDYWGQGTTVTVSS

Variant 3
                                        SEQ ID NO: 27
DIQMTQSPSSLSASLGDRATITCRASKSVSTSSYSYMHWYQQKPGQP

PKLLIKYASYLESGVPSRFSGSGSGTDFTLTISSLQPEDAATYYCQHSR
```

```
EFPWTFGGGTKVEIKRADAAPGGGGSGGGGSGGGGSEVQLVESGGG
VVQPGGSLRLSCAASGFTFSNYGMHWVRQAPEKGLEWVSYISSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKSVSTSSYSYMHWYQQKPGQPPKLLIKYASYLESGVP
SRFSGSGSGTDFTLTISSLQPEDAATYYCQHSREFPWTFGGGTKVEIK
RADAAPGGGGSGGGGSGGGGSEVQLVESGGGVVQPGGSLRLSCAAS
GFTFSNYGMHWVRQAPEKGLEWVSYISSSSTIYYADSVKGRFTISR
DNSKNTLYLQMNSLRAEDTAVYYCARRGLLLDYWGQGTTVTVSS
Variant 4
                                        SEQ ID NO: 28
DIQMTQSPSSLSASLGDRATITCRASKSVSTSSYSYMHWYQQKPGQP
PKLLIKYASYLESGVPSRFSGSGSGTDFTLTISSLQPEDAATYYCQHSR
EFPWTFGGGTKVEIKRADAAPGGGGSGGGGSGGGGSEVQLVESGGG
DVKPGGSLRLSCAASGFTFSNYGMHWVRQAPEKGLEWVSYISSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKSVSTSSYSYMHWYQQKPGQPPKLLIKYASYLESGVP
SRFSGSGSGTDFTLTISSLQPEDAATYYCQHSREFPWTFGGGTKVEIK
RADAAPGGGGSGGGGSGGGGSEVQLVESGGGDVKPGGSLRLSCAAS
GFTFSNYGMHWVRQAPEKGLEWVSYISSSSTIYYADSVKGRFTISR
DNSKNTLYLQMNSLRAEDTAVYYCARRGLLLDYWGQGTTVTVSS
Variant 6
                                        SEQ ID NO: 29
DIQMTQSPSSLSASLGDRATITCRASKSVSTSSYSYMHWYQQKPGQA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
LVQPGGSLRLSCAASGFTFSNYGMHWVRQAPGKGLEWVSYISSSST
IYYADSVKGRFTISRDNAKNSLYLQMNSLRAEDTAVYYCARRGLLL
DYWGQGTTVTVSSASTKGPSVFPLAPLESSGSDIQMTQSPSSLSASLG
DRATITCRASKSVSTSSYSYMHWYQQKPGQAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGLVQPGGSLRLSCAAS
GFTFSNYGMHWVRQAPGKGLEWVSYISSSSTIYYADSVKGRFTISR
DNAKNSLYLQMNSLRAEDTAVYYCARRGLLLDYWGQGTTVTVSS
Variant 7
                                        SEQ ID NO: 30
DIQMTQSPSSLSASLGDRATITCRASKSVSTSSYSYMHWYQQKPGQA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
VVQPGGSLRLSCAASGFTFSNYGMHWVRQAPEKGLEWVSYISSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKSVSTSSYSYMHWYQQKPGQAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGVVQPGGSLRLSCAAS
GFTFSNYGMHWVRQAPEKGLEWVSYISSSSTIYYADSVKGRFTISR
DNSKNTLYLQMNSLRAEDTAVYYCARRGLLLDYWGQGTTVTVSS
Variant 8
                                        SEQ ID NO: 31
DIQMTQSPSSLSASLGDRATITCRASKSVSTSSYSYMHWYQQKPGQA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
DVKPGGSLRLSCAASGFTFSNYGMHWVRQAPEKGLEWVSYISSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKSVSTSSYSYMHWYQQKPGQAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGDVKPGGSLRLSCAAS
GFTFSNYGMHWVRQAPEKGLEWVSYISSSSTIYYADSVKGRFTISR
DNSKNTLYLQMNSLRAEDTAVYYCARRGLLLDYWGQGTTVTVSS
Variant 10
                                        SEQ ID NO: 32
DIQMTQSPSSLSASVGDRVTITCRASKSVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
LVQPGGSLRLSCAASGFTFSNYGMHWVRQAPGKGLEWVSYISSSST
IYYADSVKGRFTISRDNAKNSLYLQMNSLRAEDTAVYYCARRGLLL
DYWGQGTTVTVSSASTKGPSVFPLAPLESSGSDIQMTQSPSSLSASVG
DRVTITCRASKSVSTSSYSYMHWYQQKPGKAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGLVQPGGSLRLSCAAS
GFTFSNYGMHWVRQAPGKGLEWVSYISSSSTIYYADSVKGRFTISR
DNAKNSLYLQMNSLRAEDTAVYYCARRGLLLDYWGQGTTVTVSS
Variant 11
                                        SEQ ID NO: 33
DIQMTQSPSSLSASVGDRVTITCRASKSVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
VVQPGGSLRLSCAASGFTFSNYGMHWVRQAPEKGLEWVSYISSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASVG
DRVTITCRASKSVSTSSYSYMHWYQQKPGKAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGVVQPGGSLRLSCAAS
GFTFSNYGMHWVRQAPEKGLEWVSYISSSSTIYYADSVKGRFTISR
DNSKNTLYLQMNSLRAEDTAVYYCARRGLLLDYWGQGTTVTVSS
```

Variant 12
SEQ ID NO: 34
DIQMTQSPSSLSASVGDRVTITCRASKSVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
DVKPGGSLRLSCAASGFTFSNYGMHWVRQAPEKGLEWVSYISSSSST
IYYADSVKGRFTISRDNSKNTLYLQMNSLRAEDTAVYYCARRGLLL
DYWGQGTTVTVSSASTKGPSVFPLAPLESSGSDIQMTQSPSSLSASVG
DRVTITCRASKSVSTSSYSYMHWYQQKPGKAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGDVKPGGSLRLSCAAS
GFTFSNYGMHWVRQAPEKGLEWVSYISSSSSTIYYADSVKGRFTISR
DNSKNTLYLQMNSLRAEDTAVYYCARRGLLLDYWGQGTTVTVSS Variant 13
SEQ ID NO: 35
DIQMTQSPSSLSASLGDRATITCRASKTVSTSSYSYMHWYQQKPGQP
PKLLIKYASYLESGVPSRFSGSGSGTDFTLTISSLQPEDAATYYCQHSR
EFPWTFGGGTKVEIKRADAAPGGGGSGGGGSGGGGSEVQLVESGGG
LVQPGGSLRLSCAASGFTFSNYGMHWVRQAPGKGLEWVSYISSGSST
IYYADSVKGRFTISRDNAKNSLYLQMNSLRAEDTAVYYCARRGLLL
DYWGQGTTVTVSSASTKGPSVFPLAPLESSGSDIQMTQSPSSLSASLG
DRATITCRASKTVSTSSYSYMHWYQQKPGQPPKLLIKYASYLESGVP
SRFSGSGSGTDFTLTISSLQPEDAATYYCQHSREFPWTFGGGTKVEIK
RADAAPGGGGSGGGGSGGGGSEVQLVESGGGLVQPGGSLRLSCAAS
GFTFSNYGMHWVRQAPGKGLEWVSYISSGSSTIYYADSVKGRFTISR
DNAKNSLYLQMNSLRAEDTAVYYCARRGLLLDYWGQGTTVTVSS Variant 14
SEQ ID NO: 36
DIQMTQSPSSLSASLGDRATITCRASKTVSTSSYSYMHWYQQKPGQP
PKLLIKYASYLESGVPSRFSGSGSGTDFTLTISSLQPEDAATYYCQHSR
EFPWTFGGGTKVEIKRADAAPGGGGSGGGGSGGGGSEVQLVESGGG
VVQPGGSLRLSCAASGFTFSNYGMHWVRQAPEKGLEWVSYISSGSS
TIYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKTVSTSSYSYMHWYQQKPGQPPKLLIKYASYLESGVP
SRFSGSGSGTDFTLTISSLQPEDAATYYCQHSREFPWTFGGGTKVEIK
RADAAPGGGGSGGGGSGGGGSEVQLVESGGGVVQPGGSLRLSCAAS
GFTFSNYGMHWVRQAPEKGLEWVSYISSGSSTIYYADSVKGRFTISR
DNSKNTLYLQMNSLRAEDTAVYYCARRGLLLDYWGQGTTVTVSS Variant 15
SEQ ID NO: 37
DIQMTQSPSSLSASLGDRATITCRASKTVSTSSYSYMHWYQQKPGQP
PKLLIKYASYLESGVPSRFSGSGSGTDFTLTISSLQPEDAATYYCQHSR
EFPWTFGGGTKVEIKRADAAPGGGGSGGGGSGGGGSEVQLVESGGG
DVKPGGSLRLSCAASGFTFSNYGMHWVRQAPEKGLEWVSYISSGSS
TIYYADSVKGRFTISRDNSKNTLYLQMNSLRAEDTAVYYCARRGLLL
DYWGQGTTVTVSSASTKGPSVFPLAPLESSGSDIQMTQSPSSLSASLG
DRATITCRASKTVSTSSYSYMHWYQQKPGQPPKLLIKYASYLESGVP
SRFSGSGSGTDFTLTISSLQPEDAATYYCQHSREFPWTFGGGTKVEIK
RADAAPGGGGSGGGGSGGGGSEVQLVESGGGDVKPGGSLRLSCAAS
GFTFSNYGMHWVRQAPEKGLEWVSYISSGSSTIYYADSVKGRFTISR
DNSKNTLYLQMNSLRAEDTAVYYCARRGLLLDYWGQGTTVTVSS Variant 16
SEQ ID NO: 38
DIQMTQSPSSLSASVGDRVTITCRASKTVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
LVQPGGSLRLSCAASGFTFSNYGMHWVRQAPGKGLEWVSYISSGSS
TIYYADSVKGRFTISRDNAKNSLYLQMNSLRAEDTAVYYCARRGLL
LDYWGQGTTVTVSSASTKGPSVFPLAPLESSGSDIQMTQSPSSLSASV
GDRVTITCRASKTVSTSSYSYMHWYQQKPGKAPKLLIKYASYLESGV
PSRFSGSGSGTDFTLTISSLQPEDFATYYCQHSREFPWTFGQGTKVEIK
RADAAPGGGGSGGGGSGGGGSEVQLVESGGGLVQPGGSLRLSCAAS
GFTFSNYGMHWVRQAPGKGLEWVSYISSGSSTIYYADSVKGRFTISR
DNAKNSLYLQMNSLRAEDTAVYYCARRGLLLDYWGQGTTVTVSS Variant 17
SEQ ID NO: 39
DIQMTQSPSSLSASVGDRVTITCRASKTVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
VVQPGGSLRLSCAASGFTFSNYGMHWVRQAPEKGLEWVSYISSGSS
TIYYADSVKGRFTISRDNSKNTLYLQMNSLRAEDTAVYYCARRGLLL
DYWGQGTTVTVSSASTKGPSVFPLAPLESSGSDIQMTQSPSSLSASVG
DRVTITCRASKTVSTSSYSYMHWYQQKPGKAPKLLIKYASYLESGVP
SRFSGSGSGTDFTLTISSLQPEDFATYYCQHSREFPWTFGQGTKVEIK
RADAAPGGGGSGGGGSGGGGSEVQLVESGGGVVQPGGSLRLSCAAS
GFTFSNYGMHWVRQAPEKGLEWVSYISSGSSTIYYADSVKGRFTISR
DNSKNTLYLQMNSLRAEDTAVYYCARRGLLLDYWGQGTTVTVSS Variant 18
SEQ ID NO: 40
DIQMTQSPSSLSASVGDRVTITCRASKTVSTSSYSYMHWYQQKPGKA
PKLLIKYASYLESGVPSRFSGSGSGTDFTLTISSLQPEDFATYYCQHSR
EFPWTFGQGTKVEIKRADAAPGGGGSGGGGSGGGGSEVQLVESGGG
DVKPGGSLRLSCAASGFTFSNYGMHWVRQAPEKGLEWVSYISSGSS
TIYYADSVKGRFTISRDNSKNTLYLQMNSLRAEDTAVYYCARRGLLL
DYWGQGTTVTVS SASTKGPSVFPLAPLESSGSDIQMTQSPSSLSASVG
DRVTITCRASKTVSTSSYSYMHWYQQKPGKAPKLLIKYASYLESGVP
SRFSGSGSGTDFTLTISSLQPEDFATYYCQHSREFPWTFGQGTKVEIK -continued
RADAAPGGGGSGGGGSGGGGSEVQLVESGGGDVKPGGSLRLSCAAS

GFTFSNYGMHWVRQAPEKGLEWVSYISSGSSTIYYADSVKGRFTISR

DNSKNTLYLQMNSLRAEDTAVYYCARRGLLLDYWGQGTTVTVSS

Variant 19

(SEQ ID NO: 41)
DIQMTQSPSSLSASLGDRATITCRASKTVSTSSYSYMHWYQQ

KPGQAPKLLIKYASYLESGVPSRFSGSGSGTDFTLTISSLQPEDFATYY

CQHSREFPWTFGQGTKVEIKRADAAPGGGGSGGGGSGGGGSEVQLV

ESGGGLVQPGGSLRLSCAASGFTFSNYGMHWVRQAPGKGLEWVSYI

SSGSSTIYYADSVKGRFTISRDNAKNSLYLQMNSLRAEDTAVYYCAR

RGLLLDYWGQGTTVTVSSASTKGPSVFPLAPLESSGSDIQMTQSPSSL

SASLGDRATITCRASKTVSTSSYSYMHWYQQKPGQAPKLLIKYASYL

ESGVPSRFSGSGSGTDFTLTISSLQPEDFATYYCQHSREFPWTFGQGT

KVEIKRADAAPGGGGSGGGGSGGGGSEVQLVESGGGLVQPGGSLRL

SCAASGFTFSNYGMHWVRQAPGKGLEWVSYISSGSSTIYYADSVKG

RFTISRDNAKNSLYLQMNSLRAEDTAVYYCARRGLLLDYWGQGTTV

TVSS 2. 5C6

5C6 induces γH2AX in BRCA2$^{(-)}$ but not BRCA2$^{(+)}$ cells and selectively suppresses the growth of the BRCA2$^{(-)}$ cells. Mechanistically, 5C6 appears to induce senescence in the BRCA2$^{(-)}$ cells. Senescence is a well-known response to DNA damage, and DNA damaging agents, including many chemotherapeutics, induce senescence after prolonged exposure (Sliwinska, et al., *Mech. Ageing Dev.*, 130:24-32 (2009); to Poele, et al., *Cancer Res.* 62:1876-1883 (2002); Achuthan, et al., *J. Biol. Chem.*, 286:37813-37829 (2011)). These observations establish that 5C6 penetrates cell nuclei and damages DNA, and that cells with preexisting defects in DNA repair due to BRCA2 deficiency are more sensitive to this damage than cells with intact DNA repair. See U.S. Published Application No. 2015/0376279.

5C6 Antibody Sequences

5C6 refers to a monoclonal anti-DNA antibody with nucleolytic activity produced by a hybridoma from MRL/lpr lupus mouse model as described in Noble et al., 2014, *Sci Rep* 4:5958 doi: 10.1038/srep05958. Mouse 5C6 sequences are provided below.

a. 5C6 Light Chain Variable Region

An amino acid sequence for the kappa light chain variable region (VL) of mAb 5C6 is:

(SEQ ID NO: 42)
DIVLTQSPASLAAVSLGERATISYRASKSVSTSGYSYMHWNQQKPGQAPRL

LIYLVSNLESGVPARFSGSGSGTDFTLNIHPVEEEDAATYYCQHIRELDTF

FGGGTKLEIK.

In some embodiments, the complementarity determining regions (CDRs) are defined accordingly to the underlining above (e.g.,

CDR L1:
(SEQ ID NO: 43)
RASKSVSTSGYSYMH;

CDR L2:
(SEQ ID NO: 44)
LVSNLES;

CDR L3:
(SEQ ID NO: 45))
QHIRELDTF.

b. 5C6 Heavy Chain Variable Region

An amino acid sequence for the heavy chain variable region (VH) of mAb 5C6 is:

(SEQ ID NO: 46)
QLKLVESGGGLVKPGGSLKLSCAASGFTFSSYTMSWVRQTPAKRLEWVATI

SSGGGSTYYPDSVKGRFTISRDNARNTLYLQMSSLRSEDTAMYYCARRAYS

KRGAMDYWGQGTSVTVSS.

In some embodiments, the complementarity determining regions (CDRs) are defined accordingly to the underlining above (e.g.,

CDR H1:
(SEQ ID NO: 47)
SYTMS;

CDR H2:
(SEQ ID NO: 48)
TISSGGGSTYYPDSVKG;

CDR H3:
(SEQ ID NO: 49))
RAYSKRGAMDY.

B. Nuclear Localization Signal Sequences

Exemplary consensus bipartite NLS include nucleoplasmin's NLS (KRPAATKKAGQAKKKK) (SEQ ID NO:58) and exemplary consensus monopartite NLS include the SV40 large T cell antigen's NLS (PKKKRKV) (SEQ ID NO:59). In some embodiments, the disclosed compositions include SEQ ID NOS:58 or 59. In some embodiments, the disclosed composition do not include a sequence or subsequence 100% identical to SEQ ID NOS: 58 or 59.

Of the humanized 3E10 variant antibodies expressly provided above, a select number were found to penetrate cell nuclei more efficiently than the original murine 3E10 (D31N) di-scFv, while others were found to have lost the ability to penetrate nuclei. In particular, variants 10 and 13 penetrated nuclei very well compared to the murine prototype.

As discussed in the Examples below, a potential bipartite nuclear localization signal (NLS) (score 4.6) was discovered in the 3E10 VL corresponding to the CDR1 and framework 2 sequences: 3E10 VL possible bipartite NLS:

(SEQ ID NO: 50)
RASKSVSTSSYSYMHWYQQKPGQPPKLLIKY

When the sequence of variant 13 was screened, the CDR1 and framework 2 sequences were again identified as a possible NLS, this time with a score of 4.8, with the S→T change present in CDR1 of variant 13 increasing the likelihood of this sequence being an NLS.

Variant 13 possible bipartite NLS:

(SEQ ID NO: 51)
RASK<u>T</u>VSTSSYSYMHWYQQKPGQPPKLLIKY

When the sequence of variant 10 was screened, the same apparent NLS was again identified. Additionally, an extended sequence involving part of framework 1, CDR1, and part of framework 2 was identified as a stronger possible NLS, this time with a score of 5.9.

Variant 10 possible bipartite NLS:

(SEQ ID NO: 52)
RVTITCRASKSVSTSSYSYMHWYQQKPGKAPKL

Thus, an exemplary consensus nuclear localization signal can be, or include, (X)RASKTVSTSSYSYMHWYQQ-KPGQPPKLL(X)KY (where (X)=any residue, but preferentially is a basic residue (R or K) (SEQ ID NO:53) or a variant thereof with at least 60, 65, 70, 75, 80, 85, 90, 95, 96, 97, 98, 99 percent sequence identity to SEQ ID NO:53.

Thus SEQ ID NOS:50-53, and fragments and variants thereof that can translocate into the nucleus of a cell alone, in the context of (i.e., grafted into) a larger amino acid sequence, conjugated to a cargo, or a combination thereof are provided and referred to herein a "NLS." In some embodiments, the NLS has at least 70, 75, 80, 85, 90, 95, 96, 97, 98, 99, or 100% amino acid sequence identity with SEQ ID NOS:50-53.

Presence of an NLS indicates that 3E10 may cross the nuclear envelope via the nuclear import pathway. In some embodiments, the NLS improves important by interacting with one or more members of the import pathway, non-limiting examples of which are discussed above. As discussed further below, follow-up studies using inhibitors of the importin pathway support this conclusion. Thus, in some embodiments, the NLS facilitates translocation into the nucleus via the importin pathway. In some embodiments, the NLS can bind to importin-β, an importin-β/importin-α heterodimer, or a combination thereof.

C. Compounds with Enhanced Nuclear Localization

The disclosed NLS can be grafted into, or conjugated to, other compounds to increase nuclear localization thereof. Thus, peptides, proteins, fusion proteins, nucleic acids, and small molecules including an NLS are provided. In some embodiment, the compound does not include or consist of one or more of murine antibodies 3E10, 5C6, G1-5, H241, and/or G2-6. In some embodiments, the compound does not include the amino acid sequence of one or more of a complete light chain variable region of 3E10, 5C6, G1-5, H241, and/or G2-6. In some embodiments, the compound does not include or consist of the amino acid sequence of one or more light chain variable regions selected from SEQ ID NOS:1, 2, 22, 23, 42, 54, 55, and 56. In some embodiments, the compound does not include or consist of the amino acid sequence of one or more light chain variable regions selected from SEQ ID NOS:20-25. In some embodiments, the compound includes an amino acid sequence at least 60, 65, 70, 75, 80, 85, 90, 95, 96, 97, 98, 99 percent identical to one or more of SEQ ID NOS:1, 2, 22, 23, 42, 54, 55, and 56, or the nuclear localization signal thereof.

1. Antibodies

In some embodiments, the compounds with enhanced nuclear localization are antibodies, or fragments or fusion proteins related thereto. The framework and CDR1 regions identified herein can be grafted into the existing target antibody, or conjugated thereto.

In some embodiments, the framework and CDR1 regions identified herein as an NLS are grafted into the antibody's existing amino acid sequence to improve the ability of the antibody to translocate into the nucleus. In preferred embodiments, the antibody is a cell-penetrating antibody. The NLS framework and CDR1 regions can be grafted into the existing antibody sequence in any suitable manner. The process can be similar to humanizing or otherwise improving the therapeutic potential of an existing antibody. Antibody humanization techniques, which are known in the art and discussed in more detail below, generally involve the use of recombinant DNA technology to manipulate the DNA sequence encoding one or more polypeptide chains of an antibody molecule. In other embodiments, the NLS sequence can be directly inserted into or substituted for an existing amino acid sequence of the same or different length.

The disclosed NLS framework and CDR1 regions, can be, but need not be, grafted directly into the corresponding framework/CDR region of the target antibody. The disclosed NLS framework and CDR1 region should be grafted into a region that improves nuclear penetration of the antibody. In some embodiments, the antibody's ability to bind to antigen is improved, or remains the same or similar, in the presence of the grafted NLS sequence. In some embodiments, for example when the antibody body is utilized as a delivery vehicle, its ability to translocate into the nucleus is preferred over its ability to bind to antibody. Thus, in some embodiments, the antibody's ability to bind to antigen is reduce or eliminated.

Antibodies can be, for example, naturally occurring in SLE patients, or obtained by screening of antibody libraries. The antibodies may be prepared by fusing spleen cells from a host having elevated serum levels of anti-DNA antibodies (e.g., MRL/1pr mice) with myeloma cells in accordance with known techniques or by transforming the spleen cells with an appropriate transforming vector to immortalize the cells. The cells may be cultured in a selective medium and screened to select antibodies that bind DNA.

In some embodiments, the antibody, variant, functional fragment or fusion protein derived therefrom can hydrolyze DNA, but this activity is not required. In some embodiments, the antibody, variant, functional fragment or fusion protein derived therefrom is cell penetrating, nuclear membrane penetrating, or both, however, these activities are not necessary. In some embodiments, the antibody, variant, functional fragment or fusion protein derived therefrom is (1) cell penetrating, (2) cell penetrating, but does not penetrate the nuclear membrane, or (3) cell penetrating and nuclear penetrating.

Thus typically, the NLS, once grafted into or conjugated to the antibody, variant, functional fragment or fusion protein, facilitates delivery of the composition across the nuclear membrane into the nucleus. In some embodiments, the compositions are delivered into the nucleus more efficiently or at a higher frequency than the antibody, variant, functional fragment or fusion protein without the disclosed NLS framework and CDR1 regions grafted into or conjugated thereto.

Antibodies that can be used include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the antibodies can contain the components of the CDRs necessary to penetrate cells, maintain DNA binding and/or interfere with DNA repair.

Also disclosed are variants and fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Exemplary fragments and fusions include, but are not limited to, single chain antibodies, single chain variable fragments (scFv), di-scFv, tri-scFv, diabody, triabody, tetrabody, disulfide-linked Fvs (sdFv), Fab', F(ab')₂, Fv, and single domain antibody fragments (sdAb). Exemplary molecules that include two or more single chain variable fragments (scFv) include, but are not limited to, divalent-scFv (di-scFv), trivalent-scFv (tri-scFv), multivalent-scFv (multi-scFv), diabodies, triabodies, tetrabodies, etc., of scFvs.

Techniques can also be adapted for the production of single-chain antibodies specific to an antigenic protein. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

The antibodies can be modified to improve their therapeutic potential. For example, the antibody can be a fusion protein containing single chain variable fragment that binds DNA or nucleosomes and a single chain variable fragment of a monoclonal antibody that specifically binds the second therapeutic target.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

The antibody can be a humanized or chimeric antibody, or a fragment, variant, or fusion protein thereof. Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule.

In some embodiments, the antibody is modified to alter its half-life. In some embodiments, it is desirable to increase the half-life of the antibody so that it is present in the circulation or at the site of treatment for longer periods of time. In other embodiments, the half-life of the antibody is decreased to reduce potential side effects. Antibody fragments are expected to have a shorter half-life than full size antibodies. Other methods of altering half-life are known and can be used in the described methods. For example, antibodies can be engineered with Fc variants that extend half-life, e.g., using Xtend™ antibody half-life prolongation technology (Xencor, Monrovia, Calif.).

The antibody subject to NLS grafting can be, for example, any antibody that binds a nuclear antigen. In some embodiments, the antibody subject to NLS grafting does not bind a nuclear antigen.

In some embodiments, the antibody subject to NLS grafting has the a heavy and/light chain sequence expressly disclosed herein. In some embodiments, the antibody subject to NLS grafting has the sequence an scFv expressly disclosed herein. Thus in some embodiments, an antibody with enhanced nuclear localization can include an amino acid sequence at least 60, 65, 70, 75, 80, 85, 90, 95, 96, 97, 98, 99 percent identical to an antibody sequence disclosed herein, or fragment thereof such as light chain.

In some embodiments, NLS grafting includes one or more substitution or insertion mutations to increase the number of basic residues on one or both sides of an NLS or a sequence in the subject antibody corresponding to an NLS. In some embodiments, the basic residues are arginine, lysine, or a combination thereof.

Preferably, mutations are made in the framework regions of the antibody subject to NLS grafting, with limited or no changes in the CDR (e.g., CDR1). Preferably, the folding of the framework(s) (e.g., frameworks 1 and 2) are preserved or otherwise remain functional.

Target regions for mutations to improve nuclear targeting of murine 3E10 are illustrated with italics and underlining in the sequence below. The NLS is illustrated with bolding (SEQ ID NO: 1)
DIVLTQSPAS_LAVSLGQRATISC_RASKSVSTSSYSYMHWYQQKPGQ_P_

_PKLLIK_YASYLESGVPARFSGSGSGTDFTLNIHPVEEEDAATYYCQH

SREFPWTFGGGTKLEIK.

Corresponding regions in other antibodies sequences can also be identified (e.g., by sequence alignment) and are thus expressly provided and can be similarly modified.

In a non-limiting example, R is substituted for C on the N-terminal end of the NLS, and K is substituted for I at the C-terminal end, improving the NLS Mapper score for the NLS from 4.6 for the original sequence to 7.6, compared to 4.6 for the original sequence.

(SEQ ID NO: 60)
DIVLTQSPASLAVSLGQRATIS<u>RR</u>ASKSVSTSSYSYMHWYQQKPGQPPKLL

<u>KK</u>YASYLESGVPARFSGSGSGTDFTLNIHPVEEEDAATYYCQHSREFPWTF

GGGTKLEIK, wherein the substitutions relative to SEQ ID NO:1 are underlined and the NLS is bolded).

In another non-limiting example T is substituted for S in CDR1 alone or in combination with the foregoing mutations. The three mutations in combination improve the NLS Mapper score to 7.8

(SEQ ID NO: 61)
DIVLTQSPASLAVSLGQRATIS<u>RR</u>ASK<u>T</u>VSTSSYSYMHWYQQKPGQPPKLL

<u>KK</u>YASYLESGVPARFSGSGSGTDFTLNIHPVEEEDAATYYCQHSREFPWTF

GGGTKLEIK, wherein the substitutions relative to SEQ ID NO:1 are underlined and the NLS is bolded).

Additionally, the underlined sequence below was identified as a putative nuclear export signal (NES) using the program NetNES.

(SEQ ID NO: 1)
DI<u>VLTQSPASLAVSL</u>GQRATISCRASKSVSTSSYSYMHWYQQKPGQPPKLL

IKYASYLESGVPARFSGSGSGTDFTLNIHPVEEEDAATYYCQHSREFPWTF

GGGTKLEIK

In some embodiments, the underlined sequence includes one or more mutations in the sequence LTQSPASLAVSL (SEQ ID NO:63) that reduces export of the compound.

2. Cargo

In some embodiments, an NLS alone, or an antibody or other protein with the NLS grafted into or conjugated thereto, is linked to an active agent cargo and used to deliver the active agent into the nucleus. In addition to conjugating the compound to the active agent, the latter can be attached to or associated with the compound by any method known in the art. Exemplary methods of linking NLS or NLS-modified protein to cargo are provided below.

Cargo includes, for example, therapeutic, nutritional, diagnostic, and prophylactic compounds. Any suitable agent may be used. Proteins, peptides, carbohydrates, polysaccharides, nucleic acid molecules, inorganic molecules, and organic molecules, as well as diagnostic agents, can be delivered. Preferred cargos include therapeutic agents (e.g., drugs) and imaging agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, epothilones A-F, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs including mRNAs, antisense, siRNA, miRNA, anti-miRNA, piRNA, aptamers, ribozymes, external guide sequences for ribonuclease P, and triplex forming agents such as tcPNAs). In some embodiments, the active agent is a vector, plasmid, or other polynucleotide encoding an oligonucleotide such as those discussed above.

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof.

Prophylactics can include compounds alleviating swelling, reducing radiation damage, and anti-inflammatories.

For imaging, radioactive materials such as Technetium99 ($^{99m}$Tc) or magnetic materials such as $Fe_2O_3$ could be used. Examples of other materials include gases or gas emitting compounds, which are radioopaque. The most common imaging agents for brain tumors include iron oxide and gadolinium. Diagnostic agents can be radioactive, magnetic, or x-ray or ultrasound-detectable. Other detectable labels include, for example, a radioisotope, a fluorophore (e.g., fluorescein isothiocyanate (FITC), phycoerythrin (PE)), an enzyme (e.g., alkaline phosphatase, horseradish peroxidase), etc.

For example, a fluorescent label can be chemically conjugated to the nuclear penetrating compound to yield a fluorescently labeled nuclear penetrating compound. In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine and barium.

Active agents can be selected based on the type of treatment being employed.

In a particular embodiment, the cargo is p53. Thus, compositions including an antibody disclosed herein conjugated to, linked to, or otherwise associated with p53.

A recombinant fusion protein consisting of 3E10 scFv linked to p53 (referred to as Fv-p53) successfully delivered p53 into cancer cell nuclei, was selectively toxic to p53-deficient cancer cells, and inhibited growth of metastases in a p53-deficient liver metastasis model of colon cancer (Hansen, et al., *Cancer Res,* 2007; 67(4): 1769-74). A similar strategy can be employed utilizing the compounds with enhanced nuclear localization. In some embodiments, the antibody is variant 10, or 13, or a functional fragment or fusion protein thereof, or a variant thereof having at least 60, 65, 70, 75, 80, 85, 90, 95, 96, 97, 98, or 99 percent sequence identity to variant 10 or 13, or a light chain or scFv thereof (e.g., SEQ ID NOS:14, 22, 32, 17, 23, and 35). Such compound would be particularly useful for treating diseases and conditions characterized by reduced or mutated p53 such basal-like triple negative breast cancer.

3. Method of Making Conjugates, Fusions, and Linkages

Exemplary methods of makings conjugates, fusions and linkages including a nuclear penetrating compound as also provided. For example, the NLS alone, or an antibody or other protein, or a fragment or fusion protein thereof, with the NLS grafted therein, can be expressed in a host cell as a fusion protein additionally containing a biologically active polypeptide. A monoclonal antibody, or active fragment thereof, can be chemically linked to a polypeptide by a peptide bond or by a chemical or peptide linker molecule of the type well known in the art. Methods for attaching a drug or other small molecule pharmaceutical to a polypeptides including antibody fragments are well known and can include use of bifunctional chemical linkers such as N-succinimidyl (4-iodoacetyl)-aminobenzoate; sulfosuccinimidyl (4-iodoacetyl)-aminobenzoate; 4-succinimidyl-oxycarbonyl-.A-inverted.-(2-pyridyldithio) toluene; sulfosuccinimidyl-6-[.alpha.-methyl-.A-inverted.-(pyridyldithiol)-toluami-do] hexanoate; N-succinimidyl-3-(-2-pyridyldithio)-proprionate; succinimidyl-6-[3 (–(-2-pyridyldithio)-proprionamido] hexanoate; sulfosuccinimidyl-6-[3 (–(-2-pyridyldithio)-propionamido] hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are discussed in, for example, U.S. Pat. Nos. 5,349,066, 5,618,528, 4,569,789, 4,952,394, and 5,137,877.

The linker can be cleavable or noncleavable. Highly stable linkers can reduce the amount of payload that falls off in circulation, thus improving the safety profile, and ensuring that more of the payload arrives at the target cell. Linkers can be based on chemical motifs including disulfides, hydrazones or peptides (cleavable), or thioethers (noncleavable) and control the distribution and delivery of the active agent to the target cell. Cleavable and noncleavable types of linkers have been proven to be safe in preclinical and clinical trials (see, e.g., Brentuximab vedotin which includes an enzyme-sensitive linker cleavable by cathepsin; and Trastuzumab emtansine, which includes a stable, non-cleavable linker). In particular embodiments, the linker is a peptide linker cleavable by Edman degredation (Banchor, et al., *Molecular diversity*, 17 (3): 605-11 (2013)).

A non-cleavable linker can keep the active agent within the cell or the target microenvironment. As a result, the entire polypeptide, linker and active agent enter the targeted cell where the polypeptide is degraded to the level of an amino acid. The resulting complex between the amino acid of the polypeptide, the linker and the active agent becomes the active drug. In contrast, cleavable linkers are catalyzed by enzymes in the target cell or microenvironment where it releases the active agent. Once cleaved, the payload can escape from the targeted cell and attack neighboring cells (also referred to as "bystander killing"). In some cases, cleavage of the linker can lead to two active agents, the antibody itself and its payload, which can have different mechanisms of action in the target cell or microenvironment.

In some embodiments, there is one or more additional molecules, between the active agent and the cleavage site. Other considerations include site-specific conjugation (TDCs) (Axup, *Proceedings of the National Academy of Sciences*, 109 (40): 16101-6 (2012) and conjugation techniques such as those described in Lyon, et al., *Bioconjugate Chem.*, 32 (10): 1059-1062 (2014), and Kolodych, et al., *Bioconjugate Chem.*, 26 (2): 197-200 (2015) which can improve stability and therapeutic index, and α emitting immunoconjugates (Wulbrand, et al., Multhoff, Gabriele, ed., *PLoS ONE*. 8 (5): e64730 (2013)).

The composition can be referred to as an antibody drug conjugate (ADC). The active agent can be, for example, a chemotherapeutic drug. By combining the targeting of the antibody with the cancer-killing ability of cytotoxic drugs, ADCs allow sensitive discrimination between healthy and diseased tissue.

D. Pharmaceutical Compositions

The disclosed compounds can be formulated with appropriate pharmaceutically acceptable carriers into pharmaceutical compositions for administration to an individual in need thereof. The formulations can be administered enterally (e.g., oral) or parenterally (e.g., by injection or infusion).

The disclosed compositions can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

In some embodiments, the disclosed compositions are administered systemically by, for example, injection or infusion. In some embodiments, the compositions are administered locally by injection or infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin. In many cases, isotonic agents, for example, sugars or sodium chloride are included.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, exemplary methods of preparation include vacuum-drying and freeze-drying techniques which yield a powder of the active ingredient plus any additional desired ingredient from a previously sterile-filtered solution thereof.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Exemplary hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition, which may include plasticizers, pigments, colorants, stabilizing agents, and glidants. Formulations can be prepared using one or more pharmaceutically acceptable excipients, including diluents, preservatives, binders, lubricants, disintegrators, swelling agents, fillers, stabilizers, and combinations thereof.

Controlled release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

III. Method of Use

Methods of using the disclosed compositions are also provided.

A. Methods of Increasing Nuclear Translocation of Active Agents

Methods for transporting an active agent into the nucleus of a target cell are provided. Typically the target cells are contacted with a compound having the active agent linked to the NLS alone, or to an antibody, or fragment or fusion protein with the NLS grafted into or conjugated thereto. In some embodiments, the antibody having the NLS grafted into or conjugated thereto is the active agent and is free from additional cargo. The contacting can occur in vitro, or in vivo following administration of the compound to a subject in need thereof. By this method, the biologically active molecule is transported into the nucleus of the target cell.

In some embodiments, this method is utilized in vitro as part of a larger method to characterize an activity or effect of the active agent on the cells. The activity can be, for example, enhanced cell growth, reduced cell growth, apoptosis, enhanced cell signaling or secretion of a particular type or generally, or reduced signaling or secretion of a particular type or generally. In some embodiments, a series of different active agents are linked to a compound with enhanced nuclear translocation, and each is separately contacted with cells. Compounds having the desired activity or lack of an undesired activity can be selected. Those compounds that are selected or otherwise pass this screening test can then be further utilized in additional screening tests in vivo to determine such attributes of selected molecules as in vivo function, (e.g., side effects and safety).

B. Methods of Treatment

The disclosed compositions can also be utilized in therapeutic, diagnostic, and prophylactic methods. Typically, such methods include administering to a subject in need thereof an effective amount of an active agent linked to the NLS alone, or to an antibody, fragment, or fusion protein with the NLS grafted into or conjugated thereto. The active agent is typically selected based on the desired therapy (e.g., enhances cell growth, reduces cell growth, apoptosis, enhances cell signaling or secretion of a particular type or generally, reduces signaling or secretion of a particular type or generally, etc.). In some embodiments, the antibody having the NLS grafted into or conjugated thereto is the active agent and is free from additional cargo.

The compound is administered to the subject in an effective amount to accomplish the desired activity. In some embodiments, the addition of the NLS alone, or to an antibody, fragment, or fusion protein with the NLS grafted into or conjugated thereto, increases the activity of the active agent on target cells in vivo compared to the active agent alone, or reduces the dosage needed to obtain the desired result relative to the active agent alone.

As introduced above, the NLS can be grafted into a target antibody with therapeutic activity. In such embodiments, the active agent is optional, particularly when the imported or conjugated NLS sequence does not eliminate the ability of the modified antibody to bind its epitope. Typically, such methods include administering to a subject in need thereof an effective amount of an antibody with the NLS grafted into or conjugated thereto. The antibody is typically selected based on the desired therapy (e.g., hydrolyzes or otherwise damages DNA, reduces DNA damage repair, etc.). In preferred embodiments, the NLS sequence increases the translocation of the antibody into the cell's nucleus, and thereby increases or alters the biological activity of the antibody. In some embodiments, the addition of the NLS framework and CDR1 regions increases the activity antibody on target cells in vivo compared to the antibody without the NLS, or reduces the dosage needed to obtain the desired result relative to the antibody without the NLS.

C. Methods of Treating Cancer

1. Cancers to be Treated

The disclosed compositions and methods can be used to treat cancer in a subject in need thereof. In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors that may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers, such as vascular cancer such as multiple myeloma; adenocarcinomas and sarcomas of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

The disclosed compositions can be used to treat cells undergoing unregulated growth, invasion, or metastasis.

Tumor cell hypoxia is now recognized as a problem in cancer therapy because it makes cancer cells resistant to treatment with radiation and some chemotherapeutics. Hypoxia is also known to cause impaired DNA repair in cancer cells. Accordingly, in some embodiments, the disclosed compositions are used as targeted agents for hypoxic tumor cells.

As discussed above, in some embodiments, an antibody or a fragment or fusion protein having the NLS graft into or conjugated thereof can be an active agent. In some embodiments, the antibody is anti-DNA antibody. Such antibodies may be particularly usefully for treating cells with impaired DNA repair, and can be used alone or in combination with DNA damaging agents and radiotherapy. See, e.g., WO 2012/135831 and WO 2016/033321.

In some embodiments, the compositions are lethal to cells with impaired DNA repair. The cells can be defective in the expression of a gene or in the function of a protein involved in DNA repair, DNA synthesis, or homologous recombination. Exemplary genes and associated products include XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, MMS19, RAD51, RAD51B, RAD51C, RAD51D, DMC1, XRCCR, XRCC3, BRCA1, BRCA2, PALB2, RAD52, RAD54, RAD50, MRE11, NB51, WRN, BLM, KU70, KU80, ATM, ATR CHK1, CHK2, FANG family of genes, FANCA, FANCB, FANCC, FANCD1, FANCD2, FANCE, FANCF, FANCG, FANCL, FANCM, RAD1, and RAD9.

In some embodiments, the defective gene is a tumor suppressor gene. In some embodiments, the gene is associated with maintenance of chromosomal integrity and/or protection from genotoxic stress. In some embodiments, the cells are deficient in single and/or double strand break repair.

In some embodiments, the cells have one or more mutations in BRCA1, BRCA2, and/or PTEN. Gene mutations, such as BRCA1, BRCA2, PTEN mutations, can be identified using standard PCR, hybridization, or sequencing techniques.

In particular embodiments, the cancer cell is defective in DNA damage repair due to hypoxia.

Therefore, in some embodiments, the compositions can be used to treat cancers arising from DNA repair deficient familial syndromes, such as breast, ovarian, and pancreatic cancers. In these embodiments, the anti-DNA antibodies can be effective without radiotherapy or chemotherapy. For example, the compositions can be used to treat cancers that are linked to mutations in BRCA1, BRCA2, PALB2, or RAD51B, RAD51C, RAD51D, or related genes. The compositions can also be used to treat colon cancers, endometrial tumors, or brain tumors linked to mutations in genes associated with DNA mismatch repair, such as MSH2, MLH1, PMS2, and related genes. The antigen binding molecules can also be used to treat cancers with silenced DNA repair genes, such as BRCA1, MLH1, OR RAD51B, RAD51C, orRAD51D. The antigen binding molecules can also be used to treat cancers associated with chromosomal maintenance or genotoxic stress, for example, cancers in which PTEN is mutated or silences. PTEN is frequently inactivated in many cancers including breast, prostate, glioma, melanoma, and lung cancers. In these embodiments, the ability of the antigen binding molecules to inhibit DNA repair combined with the inherent repair deficiencies or other susceptibilities of these cancers can be sufficient to induce cell death.

A representative but non-limiting list of cancers that can be treating using the disclosed compositions include cancers of the blood and lymphatic system (including leukemias, Hodgkin's lymphomas, non-Hodgkin's lymphomas, solitary plasmacytoma, multiple myeloma), cancers of the genitourinary system (including prostate cancer, bladder cancer, renal cancer, urethral cancer, penile cancer, testicular cancer,), cancers of the nervous system (including mengiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer and triple negative breast cancers), and pediatric cancers (including neuroblastoma, Ewing's sarcoma, Wilms tumor, medulloblastoma).

In some embodiments, the cancer is a neoplasm or tumor that demonstrates some resistance to radiotherapy or chemotherapy. In particular embodiments, the cancer cell is resistant to radiation or chemotherapy due to hypoxia.

Cancers that are resistant to radiotherapy using standard methods include, but are not limited to, sarcomas, renal cell cancer, melanoma, lymphomas, leukemias, carcinomas, blastomas, and germ cell tumors.

2. Exemplary Active Agents for Cancer Treatment

In some embodiments, the compound with enhanced nuclear translocation includes an active agent protein, peptide, carbohydrate, polysaccharide, nucleic acid molecule, organic molecule, diagnostic active agent, or a combination thereof for treating or diagnosing cancer.

In some embodiments, the active agent is a therapeutic drug. The majority of chemotherapeutic drugs can be divided into alkylating agents, antimetabolites, anthracyclines, plant alkaloids, topoisomerase inhibitors, monoclonal antibodies, and other antitumor agents.

Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas. In some embodiments, the antineoplastic drug is a PARP inhibitor, which inhibits a step in base excision repair of DNA damage. For example, the PARP inhibitor can be Olaparib ($C_{24}H_{23}FN_4O_3$).

In some embodiments, the antineoplastic drug is a histone deacetylase inhibitor, which suppresses DNA repair at the transcriptional level and disrupt chromatin structure. In some embodiments, the antineoplastic drug is a proteasome inhibitor, which suppresses DNA repair by disruption of ubiquitin metabolism in the cell. Ubiquitin is a signaling molecule that regulates DNA repair. In some embodiments, the antineoplastic drug is a kinase inhibitor, which suppresses DNA repair by altering DNA damage response signaling pathways.

Additional antineoplastic drugs include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), some antimitotics, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide) and cytoskeletal targeting drugs such as paclitaxel.

In some embodiments the active agent is a radiosensitizer. Examples of known radiosensitizers include cisplatin, gemcitabine, 5-fluorouracil, pentoxifylline, vinorelbine, PARP inhibitors, histone deacetylase inhibitors, and proteasome inhibitors.

3. Combination Therapy

The disclosed compositions can be used in combination with standard chemotherapy, radiation therapy, and other anti-cancer treatments. Radiation therapy (a.k.a. radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. In some embodiments, the disclosed antigen binding molecules are used to increase radiosensitivity for a non-malignant condition.

Radiation therapy works by damaging the DNA of dividing cells, e.g., cancer cells. This DNA damage is caused by one of two types of energy, photon or charged particle. This damage is either direct or indirect. Indirect ionization happens as a result of the ionization of water, forming free radicals, notably hydroxyl radicals, which then damage the DNA. For example, most of the radiation effect caused by photon therapy is through free radicals. One of the major limitations of photon radiotherapy is that the cells of solid tumors become deficient in oxygen, and tumor cells in a hypoxic environment may be as much as 2 to 3 times more resistant to radiation damage than those in a normal oxygen environment.

Direct damage to cancer cell DNA occurs through high-LET (linear energy transfer) charged particles such as proton, boron, carbon or neon ions. This damage is independent of tumor oxygen supply because these particles act mostly via direct energy transfer usually causing double-stranded DNA breaks. Due to their relatively large mass, protons and other charged particles have little lateral side scatter in the tissue; the beam does not broaden much, stays focused on the tumor shape and delivers small dose side-effects to surrounding tissue. The amount of radiation used in photon radiation therapy is measured in Gray (Gy), and varies depending on the type and stage of cancer being treated. For curative cases, the typical dose for a solid epithelial tumor ranges from 60 to 70 Gy, while lymphomas are treated with lower doses. Post-operative (adjuvant) doses are typically around 45-60 Gy in 1.8-2 Gy fractions (for breast, head, and neck cancers). Many other factors are considered by radiation oncologists when selecting a dose, including whether the patient is receiving chemotherapy, patient co-morbidities, whether radiation therapy is being administered before or after surgery, and the degree of success of surgery.

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radioresistant, that is, much higher doses are required to produce a radical cure than may be safe in clinical practice. Renal cell cancer and melanoma are generally considered to be radioresistant.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radiotherapy. A third technique is to enhance the radiosensitivity of the cancer by giving certain drugs during a course of radiotherapy. In some embodiments, the disclosed compositions can accomplish techniques two, three, or a combination thereof.

D. Other Diseases to Be Treated

The foregoing compositions and methods can also be used to treat any disease or process involving events inside the nucleus. As discussed above, the cargo can be selected based on the disease to be treated. Additional exemplary diseases include, but are not limited to, Huntington's disease, Parkinson's disease. The compositions and methods can also be used for the regulation of gene expression/gene editing to treat genetic diseases, muscular dystrophies, lysosomal storage diseases, traumatic injuries.

EXAMPLES

Example 1: Nuclear Uptake of Variant 13 is Independent of Endocytosis

Materials and Methods

Reagents

Unless otherwise stated, all cell culture reagents were obtained from Invitrogen (Carlsbad, Calif., USA). Dynasore, Methyl beta-cyclodextrin, EIPA, Chlorpromazine, Ivermectin, Importazole, leptomycin B, Filipin, and Mifepristone were purchased from Sigma Aldrich. Concentrated stock solutions of all compound were prepared either in DMSO or PBS. For all pre-incubation experiments, the target final concentration of drug was prepared in the respective cell culture medium, and sterile-filtered immediately prior to experimentation. Protein L, protein L primary antibody and goat, anti-chicken secondary antibodies were acquired from Invitrogen.

Cells

DLD-1 colon cancer cells (Horizon Discovery Ltd) were cultivated in RPMI1640 containing 10% v/v FBS, and A549 lung carcinoma cells (ATCC) and MCF7 breast cancer cells (ATCC) were maintained in high-glucose DMEM supplemented with 10% v/v FBS. All cell lines were maintained in a pre-humidified atmosphere containing 5% v/v CO2 and used within ten passages.

Variant 13 Protein Expression and Purification

3E10 antibody sequences are provided above. Expression and purification of variant 13 (e.g., SEQ ID NOS:17, 23, and 35) from a CHO cell system was performed using a previously-described approach (Rattray et al., *Biochem Biophys Res Commun* 496, 858-864 (2018)). Purity and stability of variant 13 was verified using a combination of SDS-PAGE, and size-exclusion chromatography (SEC-HPLC).

Protein L Immunodetection of Antibody Cell Penetration

For all experiments, cells were cultivated overnight to allow for attachment, followed by pretreatment with either control medium (absence of inhibitor), or medium containing inhibitor for durations previously-reported in the literature (see Table 1, below).

TABLE 1

Inhibitors

| COMPOUND | ABBREV. | CONCENTRATION (µM) | DURATION (HOURS) | EFFECTOR/ TRAFFICKING MECHANISM | REF. |
|---|---|---|---|---|---|
| CHLORPROMAZINE | CPZ | 10-100 | 1 | AP2, CME | Dutta, et al., *Cell. Log.*, 2: 203-208 (2012) |
| DYNASORE | Dyn | 10-100 | 1 | CME, dynamin GTPase inhibitor | Macia et al., *Dev. Cell*, 10: 839-850 (2006) |
| METHYL-B-CYCLODEXTRIN | MβCD | 5,000-10,000 | 1 | Cholesterol sequestration, CIE | Dutta, et al., *Cell. Log.*, 2: 203-208 (2012) |
| 5-(N-ETHYL-N-ISOPROPYL)-AMILORIDE | EIPA | 10-100 | 1 | $Na^+/H^+$ exchange, Macropinocytosis | Gekle et al., *J of Physio.*, 520: 709-721 (1999). |
| SODIUM AZIDE | $NaN_3$ | 10,000-100,000 | 0.5-1 | Energy-dependent | Cooper, et al., *J. Biol. Chem.*, 281: 16563-16569 (2006) |
| TEMPERATURE | T | N/A | 0.5-1 | Energy-dependent | |
| LEPTOMYCIN B | LMB | 0.001-0.02 | 1-4 | CRM1, Nuclear export | van der Watt et al., *Mol. Can. Ther.*, 15: 560-573 (2016), Lundberg et al., *Antiviral Res.*, 100: 662-672 (2013) |
| IVERMECTIN | — | 10-100 | 1-4 | Importin α/β, Nuclear import | (Wagstaff et al., *Biochem. J.*, 443, 851-856 (2012), van der Watt et al., *Mol. Can. Ther.*, 15: 560-573 (2016) |
| MIFEPRISTONE | — | 10-200 | 1-4 | Importin α/β-NLS interaction, Nuclear import | Lundberg et al., *Antiviral Res.*, 100: 662-672 (2013), Wagstaff et al., *J. of Biom. Screen.*, 16, 192-200 (2011) |

TABLE 1-continued

Inhibitors

| COMPOUND | ABBREV. | CONCENTRATION (µM) | DURATION (HOURS) | EFFECTOR/ TRAFFICKING MECHANISM | REF. |
|---|---|---|---|---|---|
| IMPORTAZOLE | — | 10-100 | 1-4 | Nuclear import | Soderholm et al., *ACS Chem. Bio.*, 6, 700-708 (2011) |

For endocytosis inhibition experiments, cells were cultivated in serum-free medium containing 1% v/v BSA to deplete endogenous serum levels. Following preincubation with inhibitors, cells were treated with either control medium or 10 µM variant 13, and the same dose of small molecule inhibitor for a further 30 minutes. For all experiments, cells were washed thrice, followed by immediate fixation with pre-chilled ice-cold ethanol. Subsequently, treated cells were probed using a protein L immunodetection approach to probe variant 13 nuclear uptake (Rattray et al., *Biochem Biophys Res Commun* 496, 858-864 (2018)). All monolayers were immediately imaged following color development on an Evos Fl microscope.

Results

Previous reports have considered the role of energy-dependent, endocytic trafficking in cellular uptake of ANAs. A panel of small molecule inhibitors of clathrin-dependent and -independent endocytosis were used to test the role of endocytosis in variant 13 cellular and nuclear penetration. Doses of inhibitors used in this study were selected to ensure minimal toxicity to the cells. Cells were pre-treated with inhibitors prior to the addition of variant 13 and evaluation of its cellular penetration by protein L immunostain. The results indicate that inhibition of endocytosis did not impact variant 13 cellular and nuclear penetration.

Example 2: The Sequence of 3E10 VL has a Putative Bipartite Classic Nuclear Localization Signal Materials and Methods In Silico Prediction of Nuclear Localization Sequences The "cNLS Mapper" program, an opensource in silico NLS prediction software, was used to screen for any sequences that may be similar to classic nuclear localization signals (NLS). A cut-off score of 4.0 was selected (higher values correlate with increased likelihood of representing an NLS). This program is based on Kosugi et al., (2009) *PNAS*, 106, 10171-10176.

Amino acid sequences of antibody VH and VL were input into online cNLS Mapper. NLS Mapper does not rely on comparison with cNLS sequence libraries, but uses contribution scores from amino acid to predict potential cNLS presence within an amino acid sequence (Kosugi et al., *Proc Natl Acad Sci USA* 106, 10171-10176 (2009)). G1-5 sequence is available at Genbank AF289183.1. H241, G2-6, 2C10, and G5-8 sequences are presented in reference (Im et al., *Mol Immunol* 67, 377-387 (2015)). 3D8 sequence is available in patent WO 2010/056043.

3E10 Sequences

3E10 sequences are provided above. The analysis below is focused on humanized variant 10 (e.g., SEQ ID NOS:14, 22, and 32) and variant 13 (e.g., SEQ ID NOS:17, 23, and 35).

Results

A range of humanized 3E10 variants were generated with subtle differences in framework and CDR sequences. In evaluating the ability of these variants to carry out the original functions of 3E10 (D31N) di-scFv, a select number of the variants were found to penetrate cell nuclei more efficiently than the original 3E10 (D31N) di-scFv, while others were found to have lost the ability to penetrate nuclei. In particular, variants 10 and 13 penetrated nuclei very well compared to the prototype. The sequences of the VL and VH of 3E10 and the new variants were compared to determine if key changes could be identified that are responsible for an increase in efficiency of nuclear penetration.

The NLS Mapper software, which screens and scores amino acid sequences for potential classic NLS sequences (Kosugi et al., *Proc Natl Acad Sci USA* 106, 10171-10176 (2009)), was used to evaluate the 3E10 VH and VL. The entire sequences were analyzed, with a cut-off score of 4.0 (higher scores equate to greater probability of a cNLS). Under these parameters, no cNLS was predicted in the 3E10 VH sequence. However, a potential bipartite cNLS with score 4.6 was found in the 3E10 VL sequence, spanning the CDR1, framework 2, and first amino acid of CDR2 (Table 2).

3E10 VL possible bipartite NLS:

```
                                    (SEQ ID NO: 50)
RASKSVSTSSYSYMHWYQQKPGQPPKLLIKY
    ‾
```

When the sequence of variant 13 was screened, the CDR1 and framework 2 sequences were again identified as a possible NLS, this time with a score of 4.8, with the S→T change present in CDR1 of variant 13 increasing the likelihood of this sequence being an NLS.

Variant 13 possible bipartite NLS:

```
                                    (SEQ ID NO: 51)
RASKTVSTSSYSYMHWYQQKPGQPPKLLIKY
    ‾
```

When the sequence of variant 10 was screened, the same apparent NLS was again identified. Additionally, an extended sequence involving part of framework 1, CDR1, and part of framework 2 was identified as a stronger possible NLS, this time with a score of 5.9.

Variant 10 possible bipartite NLS:

```
                                    (SEQ ID NO: 52)
RVTITCRASKSVSTSSYSYMHWYQQKPGKAPKL
```

The sequence of 3E10 VL has a putative bipartite classic nuclear localization signal that is relatively conserved across a panel of known nuclear-penetrating anti-DNA autoantibodies. Identification of a possible bipartite NLS in 3E10 has important implications in understanding the mechanism by which 3E10 localizes to the nucleus. Presence of an NLS indicates that 3E10 may cross the nuclear envelope via the nuclear import pathway, and as discussed further below, follow-up studies using inhibitors of the importin pathway support this conclusion. From a technology perspective, identification of key sequences in framework and CDR1 regions of the 3E10 VL provides the opportunity for CDR and framework grafting of these sequences onto other antibodies with the goal of conferring nuclear-penetrating ability to such antibodies, and this may be useful in strategies for re-engineering antibodies for use in therapeutic applications.

An NIH Basic Local Alignment Search Tool search on this putative cNLS yielded many anti-DNA antibody matches, and similar sequences were identified in the VL of several other known nuclear-localizing anti-dsDNA autoantibodies. Specifically, cNLS Mapper identified nearly identical putative cNLS sequences in VL of the nuclear-localizing G1-5, G2-6, and H241 anti-dsDNA autoantibodies. In contrast, this sequence is absent in anti-dsDNA autoantibodies that are known to depend on VH for nuclear localization (2C10), that localize in the cytoplasm (3D8), or that cannot penetrate cells (G5-8) (Im et al., *Mol Immunol* 67, 377-387 (2015), Lee et al., *Biorg Med Chem* 15, 2016-23 (2007); Kim et al., *J Biol Chem* 281, 15287-95 (2006); Yang et al., *Cell Mol Life Sci* 66, 1985-97 (2009)) (Table 2). Taken together, these findings are supportive of a potential cNLS motif that is conserved within the sequence of some nuclear-penetrating anti-dsDNA autoantibodies.

TABLE VL Sequences of cell-penetrating anti-DNA autoantibodies. CDR1 + framework 2 sequence are in bold. Additional important sequence for variant 10 is in bold/italics. The VL and VH amino acid sequences of anti-dsDNA autoantibodies that localize to nuclei (3E10, G1-5, H241, G2-6, and 2C10), localize to cytoplasm (3D8), or cannot penetrate cells (G5-8) were screened for the presence of a cNLS by cNLS Mapper, with cutoff score 4.0. A nearly identical potential bipartite cNLS was identified in VL of all of the nuclear-localizing antibodies except 2C10, which is known to use VH for cellular penetration (Im et al., *Mol Immunol* 67, 377-387 (2015)).

| Name/Source | VL/Potential VL cNLS Sequence (bold with underlining) | VL cNLS? | Nuclear localizing? |
| --- | --- | --- | --- |
| 3E10 MRL/lpr | DIVLTQSPASLAVSLGQRATISCRASKSV STSSYSYMHWYQQKPGQPPKLLIKYA SYLESGVPARFSGSGSGTDFTLNIHPVEE EDAATYYCQHSREFPWTFGGGTKLEIK (SEQ ID NO: 1) | Yes | Yes |
| Var 13 Humanized | DIQMTQSPSSLSASLGDRATITCRASKTV STSSYSYMHWYQQKPGQPPKLLIKYA SYLESGVPSRFSGSGSGTDFTLTISSLQPE DAATYYCQHSREFPWTFGGGTKVEIK (SEQ ID NO: 23) | Yes | Yes |
| Var 10 Humanized | DIQMTQSPSSLSASVGD***RVTITC*RASKSV STSSYSYMHWYQQKPGKAPKL**LIKYA SYLESGVPSRFSGSGSGTDFTLTISSLQPE DFATYYCQHSREFPWTFGQGTKVEIK (SEQ ID NO: 22) | Yes | Yes |
| 5C6 MRL/lpr | DIVLTQSPASLAAVSLGERATISYRASKS VSTSGYSYMEWNQQKPGQAPRLLIYL VSNLESGVPARFSGSGSGTDFTLNIHPVE EEDAATYYCQHFRELDTFFGGGYKLEIK (SEQ ID NO: 42) | Yes | Yes |
| G1-5 MRL/lpr GenBank AF289183.1 | DVVMTQSPASLAVSLGQRATISCRASKS VSTSSYNYMHWHQQKPGQPPKLLIKYA SYLESGVPARFSGSGSGTDFTLNIHPVE EEDAATYYCHHSREFPWTFGGGTKLEIK RA (SEQ ID NO: 55) | Yes | Yes |
| H241 | RASKSVSTSNYSYMYWYQQKPGQPPK LLIKY (SEQ ID NO: 54) | Yes | Yes |
| G2-6 | RASKSVSTSSYNYIHWHQQKPGQPPKL LIKY (SEQ ID NO: 56) | Yes | Yes |
| 2C10 | — | No (uses VH) | Yes |
| 3D8 MRL/lpr Genbank K3939261.1 | DLVMSQSPSSLAVSAGEKVTMSCKSSQS LFNSRTRKNYLAWYQQKPGQSPKLLI YWASTRESGVPDRFTGSGSGTDFTLTISS VQAEDLAVYYCKQSYYHMYTFGSGTKL EIK (SEQ ID NO: 57) | No | No, localizes to cytoplasm |

TABLE VL Sequences of cell-penetrating anti-DNA autoantibodies. CDR1 + framework 2 sequence are in bold. Additional important sequence for variant 10 is in bold/italics. The VL and VH amino acid sequences of anti-dsDNA autoantibodies that localize to nuclei (3E10, G1-5, H241, G2-6, and 2C10), localize to cytoplasm (3D8), or cannot penetrate cells (G5-8) were screened for the presence of a cNLS by cNLS Mapper, with cutoff score 4.0. A nearly identical potential bipartite cNLS was identified in VL of all of the nuclear-localizing antibodies except 2C10, which is known to use VH for cellular penetration (Im et al., *Mol Immunol* 67, 377-387 (2015)).

| Name/Source | VL/Potential VL cNLS Sequence (bold with underlining) | VL cNLS? | Nuclear localizing? |
|---|---|---|---|
| 4H2 MRL/lpr | DIVLTQSPATLSVTPGDRVSLSCRASQSI SNYLHWYQQKSHESPRLLIKYASQSIS GIPSRFSGSGSGTDFTLSIISVETEDFGMY FCQQSNSWPLTFGAGTKLELK (SEQ ID NO: 62) | No | No, localizes to cytoplasm |
| G5-8 | — | No | No, cannot penetrate cells |

Example 3: Ivermectin Inhibits Nuclear Penetration by Variant 13 and Human SLE Antibodies Materials and Methods DLD-1 and A549 cells were treated with 10 μM variant 13 co-incubated with 0, 10, 25, or 50 μM concentrations of ivermectin. Relative intensity of protein L nuclear staining as compared to amount of stain in cells treated without ivermectin was also quantified by ImageJ.

Live MCF7 breast cancer cells were treated with control or rhodamine-labeled variant 13 (Rh-variant 13)+/−50 μM ivermectin and were then visualized under light and fluorescence microscopy. Ivermectin inhibited cellular/nuclear uptake of Rh-variant 13.

Results

3E10 scFv was previously shown to utilize the ENT2 nucleoside salvage pathway to penetrate cells (Hansen et al., *J Biol Chem* 282, 20790-20793 (2007); Wang et al., Biochem Pharmacol 86, 10.1016/j.bcp.2013.1008.1063 (2013); Boswell-Casteel and Hays, *Nucleosides Nucleotide Nucleic Acids* 36, 7-30 (2017)). Nuclear localizing signal (NLS)-like-motifs may facilitate nuclear penetration of some antinuclear antibodies (ANA) (Im et al., *Mol Immunol* 67, 377-387 (2015); Im et al., *Animal Cells and Systems* 21, 382-387 (2017); Deng et al., *Int Immunol* 12, 415-423 (2000)). NLS-based nuclear import most commonly involves the importin α/β pathway, but the role of this pathway in nuclear uptake of ANAs does not appear to have been experimentally tested previously.

The identification of a bipartite NLS in the 3E10 VL raised the possibility that the importin pathway is involved in the mechanism of nuclear localization by 3E10. Small molecule drugs including ivermectin, mifepristone, and importazole, were used to evaluate the role of the importin α/β pathway in the mechanism of variant 13 nuclear import. Ivermectin and mifepristone both inhibit the importin α/β pathway, and importazole has been reported to selectively inhibit the activity of importin β without perturbing transportin function (Wagstaff et al., *Biochem J* 443, 851-856 (2012); Wagstaff et al., *J Biomol Screen* 16, 192-200 (2011); van der Watt et al., *Mol Cancer Ther* 15, 560-573 (2016); Soderholm et al., *ACS Chem Biol* 6, 700-708 (2011); Lundberg et al., *Antiviral Res* 100, 662-672 (2013)). The impact of each inhibitor on nuclear uptake of variant 13 in DLD1 colon and A549 lung cancer cells was tested.

In this Example, the effect of ivermectin (Wagstaff et al., *Biochemical Journal* 2012 443(3): 851-856)) on the ability of variant 13 to penetrate into the nuclei of cells was evaluated. DLD1 colon cancer cells and A549 lung cancer cells were treated with variant 13 in the presence of 0-50 ivermectin. Cells were subsequently washed, fixed, and immunostained using protein L for detection of variant 13. Representative micrographs of the cells after staining demonstrated a dose-dependent reduction in nuclear penetration by variant 13 caused by ivermectin. Relative intensity of nuclear staining as compared to amount of stain in cells treated without ivermectin was also quantified by ImageJ (FIG. 1). Ivermectin also inhibited cellular/nuclear uptake of a rhodamine-labeled variant 13 into MCF7 breast cancer cells.

Example 4: Importazole Inhibits Nuclear Penetration by Variant 13

Materials and Methods

DLD-1 cells and A549 cells were treated with 10 μM variant 13 co-incubated with 0, 10, 25, or 50 μM concentrations of importazole and then immunostained for protein L.

Live DLD1 cancer cells were treated with control or rhodamine-labeled variant 13 (Rh-variant 13)+/−50 μM importazole and were then visualized under light and fluorescence microscopy.

Results

The identification of a bipartite NLS in the 3E10 VL raised the possibility that the importin pathway is involved in the mechanism of nuclear localization by 3E10. To test this, the effect of a nuclear import inhibitor that has been reported to have specificity for this pathway (importazole; Soderholm et al., *ACS Chem Biol* 2011 6(7): 700-8) on the ability of variant 13 to penetrate into the nuclei of DLD1 cells and A549 cells was evaluated. DLD1 and A549 cells were treated with variant 13 in the presence of 0-50 μM importazole. Cells were subsequently washed, fixed, and immunostained using protein L for detection of variant 13. Representative micrographs of the cells after staining demonstrated a reduction in nuclear penetration by variant 13 caused by importazole. Importazole also inhibited nuclear uptake of a rhodamine-labeled variant 13 into DLD1 cells.

Example 4: Mifepristone Inhibits Nuclear Penetration by Variant 13

Materials and Methods

DLD-1 cells and A549 cells were treated with 10 μM variant 13 co-incubated with 0, 10, 25, or 50 μM concentrations of mifepristone and then immunostained for protein L.

Results

The identification of a bipartite NLS in the 3E10 $V_L$ raised the possibility that the importin pathway is involved in the mechanism of nuclear localization by 3E10. To test this, the effect of a nuclear import inhibitor that has been reported to have specificity for this pathway (mifepristone; Wagstaff et al., *J Biomol Screen* 2011 16(2): 192-200) on the ability of variant 13 (Variant 13) to penetrate into the nuclei of DLD1 cells and A549 cells was evaluated. DLD1 and A549 cells were treated with variant 13 in the presence of 0-50 μM mifepristone. Cells were subsequently washed, fixed, and immunostained using protein L for detection of variant 13. Representative micrographs of the cells after staining demonstrated a reduction in nuclear penetration by variant 13 caused by mifepristone.

Example 6: Knockdown of Importin β1 Reduce 3E10 Nuclear Localization

Materials and Methods

Generation and Verification of Importin-β1 Knockdowns

Importin-β1 (KPNB1) knockdown in DLD1 cells were generated using control (D-001206-14-05) and KPNB1 (importin β1, M-017523-01-0005) siRNA (Dharmacon). DLD1 cells were seeded into 24-well (western blot) or 96-well plates (cell penetration assays) overnight. Cell monolayers were transfected with siRNA, followed by media replacement at 24 hours, and evaluation at multiple time points post-transfection. Importin β1 expression was then evaluated by western blotting of cell lysates.

Results

Figure 2:
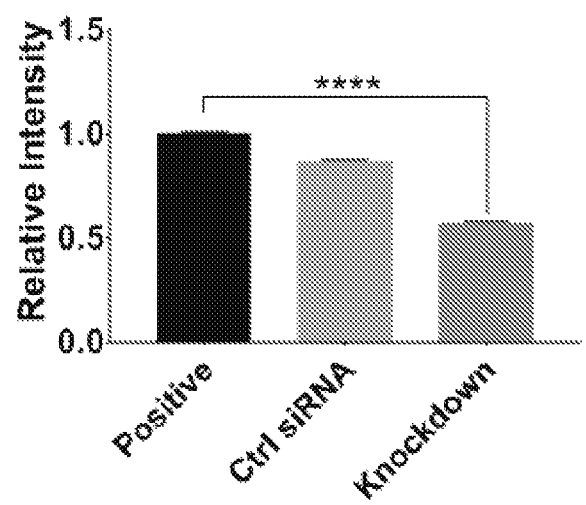
FIG. 2 is a bar graph showing quantification of relative intensity of variant 13 nuclear staining in untransfected cells with intact importin β1 (positive), cells transfected with control siRNA (Ctrl siRNA), and importin β1 knockdowns (Knockdown) after treatment with 10 μM variant 13 for 30 minutes. n=100 cells per treatment, and **** represents P≤0.001.

Knockdown of importin β1 in DLD1 cells by siRNA was next performed to further probe the role of this pathway in modulating variant 13 nuclear localization. Successful knockdown of importin β1 was confirmed by western blot, and nuclear penetration by variant 13 was then compared in untransfected cells, cells transfected with control siRNA, and cells transfected with siRNA for importin β1. A significant reduction in variant 13 signal was evident in the importin β1 knockdown cells compared to cells with intact importin β1 (FIG. 2).

The finding that three different small molecule inhibitors of the importin pathway interfere with nuclear localization by variant 13, and that siRNA-mediated knockdown of importin β1 has a similar effect, strongly implicates the importin pathway is involved in the nucleocytoplasmic shuttling of variant 13.

Example 7: Nuclear Penetration by ANAs in Human SLE Sera is Inhibited by Nuclear Import Inhibitors Materials and Methods SLE Patient Sera The McGill University Health Centre SLE clinic maintains a registry of SLE patients who undergo annual assessment. The registry, including collection and analysis of the data and samples, has the ethical approval of the MUHC institutional review board. Twenty de-identified SLE serum samples meeting study criteria were randomly selected from the total available pool for further testing.

Study criteria were intended to maximize the homogeneity of the samples and the probability of identifying a sample containing nuclear-penetrating ANAs. Inclusion criteria specified that samples were from female patients with ANA positive disease and had high levels of anti-dsDNA antibodies. Samples from patients that were taking steroid or other immunosuppressive medications (other than hydroxychloroquine) at the time of collection were excluded due to concern that these medications could reduce the probability of detecting nuclear penetrating autoantibodies. Samples from patients with a concurrent diagnosis of cancer were also excluded due to concern that malignancy may perturb autoantibody profiles.

To test the serum samples for the presence of nuclear-penetrating ANAs, MCF7 cells were treated with each sample for one hour, followed by washing, fixation, and immunostaining for IgG. Serum samples were scored positive for nuclear-penetrating antibodies if they reproducibly yielded intranuclear staining in independent experiments. Of the twenty samples, samples SLE-4, -8, -9, and -19 tested positive and were used for experimental testing.

SLE Sera Nuclear Import

DLD1 cells were pre-treated with either control media, or media containing nuclear import inhibitors for four hours. Subsequent co-treatment with inhibitor and patient SLE serum (diluted 1:50) was performed for one hour at 37° C. Following treatment, cells were fixed, blocked and probed with an alkaline-phosphatase anti-human IgG primary antibody overnight (Fisher Scientific). Cell monolayers were washed, and color developed using NBT/BCIP reagent (Fisher Scientific) for the same duration across all experiments. Following chromogen color development, all monolayers were washed, and brightfield images acquired immediately on an Evos Fl microscope.

Results

Based on the apparent conservation of the bipartite NLS in nuclear-localizing anti-DNA autoantibodies in MRL/lpr mice, experiments were designed to determine if the nuclear-localizing autoantibodies in human SLE serum would use a similar method of nuclear penetration that is dependent on the importin pathway, and that ivermectin would therefore also inhibit their ability to penetrate nuclei. Twenty SLE serum samples, labeled SLE-1-20, were screened for the presence of nuclear penetrating ANAs (Alarcon-Segovia et al., *Clin Exp Immunol* 35, 364-375 (1979); Golan et al., *J Invest Dermatol* 100, 316-322 (1993)) by anti-IgG immunostaining of treated cells. Samples SLE-4, 8, 9, and 19 were selected for further use based on their reproducible yield of strong nuclear staining in both MCF7 and DLD1 cells, consistent with the presence of nuclear-penetrating ANAs.

The ability of ivermectin to inhibit penetration by the ANAs in SLE-4, 8, 9, and 19 into DLD1 cell nuclei was next tested. Pre- and co-treatment with ivermectin reduced the nuclear staining associated with each sample, consistent with inhibition of nuclear uptake of ANAs. In addition, mifepristone and importazole were similarly found to inhibit nuclear uptake of ANAs in SLE-19 in a dose-dependent manner.

These findings show that the nucleocytoplasmic shuttling of some SLE sera autoantibodies can be blocked by treatment with inhibitors of the importin pathway.

Example 8: Nuclear Penetration by a Human Scleroderma Autoantibody is Inhibited by Ivermectin In addition to SLE, cell-penetrating autoantibodies are detected in other autoimmune diseases such as scleroderma. A panel of human scleroderma autoantibodies was screened for nuclear penetration, and one nuclear-penetrating autoantibody, SSC, was selected for testing of the effect of ivermectin on its efficiency of nuclear uptake. SSC was expressed in and purified from HEK293T cells. Microscopic analysis revealed nuclear penetration of SSC into DLD1 cells and the effect of ivermectin. Ivermectin inhibited the nuclear uptake of SSC, confirming that ivermectin can modulate the nuclear-penetrating activity of autoantibodies from multiple autoimmune diseases.

Nuclear import of macromolecules occurs via an energy-dependent process through nuclear pore complexes (Fahrenkrog and Aebi, *Nature Reviews Molecular Cell Biology* 4, 757 (2003)), and an exposed NLS in macromolecules larger than 60 kDa facilitates interaction with nuclear import machinery (Freitas and Cunha, *Current Genomics* 10, 550-557 (2009)). Nuclear import via the importin pathway proceeds with the formation of an importin-cargo complex following recognition of a NLS motif by one of several importins. Subsequently, the cargo-importin complex is recruited to the nuclear pore complex, and gains entry into the nucleus. Interaction of RanGTP with the importin-cargo complex results in cargo dissociation from importin. Herein the role of the importin pathway in variant 13 nuclear penetration was explored through incubation with a panel of known nuclear import inhibitors, and also by siRNA-mediated importin β1 knockdown studies. Both approaches demonstrated significant blockade of variant 13 nuclear penetration, confirming the involvement of the nuclear import pathway in the nuclear uptake of variant 13.

NLS-like motifs within CDR regions of nuclear-localizing ANAs have previously been proposed to be involved in their mechanism of nuclear import (Im et al., *Mol Immunol* 67, 377-387 (2015); Im et al., *Animal Cells and Systems* 21, 382-387 (2017)). Herein a potential bipartite cNLS was identified in the 3E10 VL, and this sequence is conserved in several other nuclear-localizing anti-dsDNA autoantibodies.

The identification of a possible bipartite NLS in 3E10, potentially conserved in several other anti-dsDNA antibodies, including autoantibodies from lupus (SLE), combined with the finding that an inhibitors of the importin pathway (e.g., ivermectin) inhibit nuclear localization by variant 13 indicates that the importin pathway is involved in the mechanism of nuclear localization by 3E10, and perhaps the nuclear import of many ANAs, including pathogenic ANAs in human SLE serum. Consistent with this, ivermectin, a small molecule inhibitor of the importin α/β pathway, blocked the nuclear-penetrating activity of ANAs in each of the SLE serum samples tested in the disclosed studies, and also inhibited the uptake of a nuclear-penetrating scleroderma autoantibody.

It is known that ENT2 is involved in transport of 3E10 across the cell membrane, and above-discussed findings indicate that the bipartite NLS and importin pathway aid 3E10 translocation across the nuclear envelope. Because many proteins including DNA repair enzymes utilize the importin pathway for nuclear import, the findings raise the possibility that 3E10 may perturb the import of such proteins and this may further contribute to the effect of 3E10 on DNA repair and other intranuclear functions. Another proposed mechanism for 3E10 nuclear localization is exploitation of the nuclear import of these proteins during recruitment, through association with DNA damage repair proteins in the cytoplasm.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A composition comprising a nuclear localization signal (NLS) comprising the amino acid sequence any one of SEQ ID NOS: 50-52, wherein the NLS can translocate from the cytoplasm to the nucleus of a cell, wherein the composition does not consist of an antibody comprising an amino acid sequence 100% identical to SEQ ID NOS: 1, 2, 22, 23, 42, 54, 55, and 56.

2. The composition of claim 1 wherein the NLS consists of the amino acid sequence of any one of SEQ ID NOS: 50-52.

3. The composition of claim 1 further comprising an active agent cargo linked directly or indirectly to the NLS.

4. The composition of claim 3, wherein the cargo is selected from the group consisting of proteins, peptides, carbohydrates, polysaccharides, nucleic acid molecules, inorganic molecules, and organic molecules, and diagnostic agents.

5. A composition comprising a pharmaceutically acceptable carrier and the composition of claim 1.

6. The composition of claim 5, further comprising a therapeutic agent.

7. A method of delivering a composition to the nucleus of a cell comprising contacting the cell with the composition of claim 1.

\* \* \* \* \*